US010407347B2

(12) United States Patent
Boyle et al.

(10) Patent No.: US 10,407,347 B2
(45) Date of Patent: Sep. 10, 2019

(54) SINGLE-SOURCE SYNTHESIS OF CERAMIC OXIDE NANOPARTICLES

(71) Applicant: National Technology & Engineering Solutions of Sandia, LLC, Albuquerque, NM (US)

(72) Inventors: Timothy J. Boyle, Albuquerque, NM (US); Rana Chan, Albuquerque, NM (US); Jeremiah Matthew Sears, Albuquerque, NM (US); Bernadette A. Hernandez-Sanchez, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 95 days.

(21) Appl. No.: 15/901,776

(22) Filed: Feb. 21, 2018

(65) Prior Publication Data
US 2018/0179112 A1 Jun. 28, 2018

Related U.S. Application Data

(63) Continuation-in-part of application No. 15/336,296, filed on Oct. 27, 2016.

(51) Int. Cl.
| | |
|---|---|
| *C04B 35/16* | (2006.01) |
| *B01J 13/06* | (2006.01) |
| *A61K 41/00* | (2006.01) |
| *C07F 7/02* | (2006.01) |
| *C07F 7/28* | (2006.01) |
| *C04B 35/626* | (2006.01) |
| *C04B 35/64* | (2006.01) |
| *C07F 9/00* | (2006.01) |
| *C07F 7/08* | (2006.01) |
| *B01J 13/02* | (2006.01) |
| *C01G 27/02* | (2006.01) |
| *C04B 35/628* | (2006.01) |
| *C08K 3/36* | (2006.01) |
| *C08K 3/22* | (2006.01) |

(52) U.S. Cl.
CPC .............. *C04B 35/16* (2013.01); *A61K 41/00* (2013.01); *B01J 13/02* (2013.01); *B01J 13/06* (2013.01); *C01G 27/02* (2013.01); *C04B 35/62605* (2013.01); *C04B 35/62807* (2013.01); *C04B 35/62821* (2013.01); *C04B 35/62823* (2013.01); *C04B 35/62892* (2013.01); *C04B 35/64* (2013.01); *C07F 7/02* (2013.01); *C07F 7/0836* (2013.01); *C07F 7/28* (2013.01); *C07F 9/00* (2013.01); *C08K 3/22* (2013.01); *C08K 3/36* (2013.01); *C01P 2004/84* (2013.01); *C04B 2235/3244* (2013.01); *C04B 2235/3418* (2013.01); *C04B 2235/3427* (2013.01); *C04B 2235/483* (2013.01); *C04B 2235/5445* (2013.01); *C04B 2235/656* (2013.01); *C04B 2235/94* (2013.01); *C08K 2003/2296* (2013.01)

(58) Field of Classification Search
CPC ............................. C07F 7/0821; C07F 7/0836
See application file for complete search history.

(56) References Cited

U.S. PATENT DOCUMENTS 7,033,560 B2  4/2006  Clark et al.

OTHER PUBLICATIONS

Lee, S. et al., "Atomic Layer Deposition of Hafnium Silicate Film for High Mobility Pentacene Thin Film Transistor Applications", Journal of Materials Chemistry, 2009, pp. 6857-6864, vol. 19.
Tanriverdi, S. et al., "Electrospinning and Characterization of Alumina Borosilicate Ceramic Nanofibres", Materials Science-Poland, 2007, pp. 957- 968, vol. 25.
Katayama, S. et al., "Preparation of Alkaline-Earth Metal Silicates from Gels and Their NOx-Adsorption Behavior", Journal of the European Ceramic Society, 2004, pp. 421-425, vol. 24.
Jones, S. "Amine Catalyzed Condensation of Tetraethylorthosilicate", Journal of Non-Crystalline Solids, 2001, pp. 206-210, vol. 291.
Mabuchi, T. et al., "Flourescence and Fluorescence-Excitation Spectra of Benzo(f)quinoline During the Sol-Gel-Xerogel Transitions of Mixed Silicon-Aluminum Alkoxide Systems", Bull. Chem Soc. Japan, 1993, pp. 2174-2181, vol. 66.
Samedov, K. et al., "From Molecular Gallium and Indium Siloxide Precursors to Amorphous Semiconducting Transparent Oxide Layers for Applications in Thin-Film Field-Effect Transistors", Chem Plus Chem, 2012, pp. 663-674, vol. 77.
Mehring, M. et al., "Structural Relationships in High-Nuclearity Heterobimetallic Bismuth-Oxo Clusters", European Journal of Inorganic Chemistry, 2005, pp. 4891-4901.
Kim, W-K, et al., "Atomic Layer Deposition of Hafnium Silicate Films Using Hafnium Tetrachloride and Tetra-n-butyl Orthosilicate", Journal of Vacuum Science & Technology A, 2004, pp. 1285-1289, vol. 22.

(Continued)

*Primary Examiner* — Marc S Zimmer
(74) *Attorney, Agent, or Firm* — Kevin W. Bieg

(57) ABSTRACT

The tris(trimethylsilyl)silanol (H-SST) ligand can be reacted with a Group 4 or 5 metal alkoxides in a solvent to form an SST-modified metal alkoxide precursor. Exemplary Group 4 precursors include $[Ti(SST)_2(OR)_2]$ $(OR=OPr^i, OBu^t, ONep)$; $[Ti(SST)_3(OBu'')]$; $[Zr(SST)_2(OBu^t)_2(py)]$; $[Zr(SST)_3(OR)]$ $(OR=OBu^t, ONep)$; $[Hf(SST)_2(OBu^t)_2]$; and $[Hf(SST)_2(ONep)_2(py)_n]$ $(n=1, 2)$, where $OPr^i=OCH(CH_3)_2$, $OBu^t=OC(CH_3)_3$, $OBu''=O(CH_2)_3CH_3$, $ONep=OCH_2C(CH_3)_3$, and py=pyridine. Exemplary Group 5 precursors include $[V(SST)_3(py)_2]$; $[Nb(SST)_3(OEt)_2]$; $[Nb(O)(SST)_3(py)]$; $2[H][(Nb(\mu-O)_2(SST))_6(\mu_6-O)]$; $[Nb_8O_{10}(OEt)_{18}(SST)_2 \cdot \tfrac{1}{5}Na_2O]$; $[Ta(SST)(\mu-OEt)(OEt)_3]_2$; and $[Ta(SST)_3(OEt)_2]$; where $OEt=OCH_2CH_3$. When thermally processed, the precursors can form unusual core-shell nanoparticles. For example, $HfO_2/SiO_2$ core/shell nanoparticles have demonstrated resistance to damage in extreme irradiation and thermal environments.

15 Claims, 22 Drawing Sheets

(56) References Cited

OTHER PUBLICATIONS

Trapalis, C. C. et al., "Nanostructured MeSiO2 (Me=Ag, Cu) Coatings with Antibacterial Activity", Springer: Dordrecht, Netherlands, 2003, Chapter 1 of "Nanostructured Materials and Coatings for Biomedical and Sensor Applications", pp. 41-49.

Gilman, H. et al., "Highly Branched-Chain Methylhalo Polysilanes", J. Organometal. Chem., 1966, pp. 199-200, vol. 5.

Kornev, A. N. et al., Lithium and Sodium Tris(trimethylsilyl)Silanolates. Synthesis and Reactivity, Russian Chemical Bulletin, 1995, pp. 1107-1109, vol. 44.

Boo, B. H. et al., Spectroscopic and AM1 Semiempirical Studies of Vibrations of Tris(Trimethylsilyl) Silane Derivatives, (Me3Si)3SiX (X=H, Cl, OH, OD, ME, OMe, SiMe3), Journal of Organometallic Chemistry, 1992, pp. 1-9, vol. 436.

Chesnokova, T. A. et al. "Cobalt(II) and Iron(II) Tris(Trimethylsilyl)Siloxides: Synthesis, Structure and Reactivity", Journal of Organometallic Chemistry, 2002, pp. 20-31, vol. 642.

Kornev, A. N. "Ferrous Tris(Trimethylsilyl)Silanolates: Synthesis, Structure, Reactivity and Thermal Decomposition", Journal of Organometallic Chemistry, 1997, pp. 113-119, vol. 547.

Wu, Z. et al., "Synthesis of Tantalum(V) Amido Silyl Complexes and the Unexpected Formation of (Me2N)3Ta(n2-ONMe2)[OSi(SiMe3)3] from the Reaction of (Me2N)4Ta[Si(SiMe3)3] with O2", Organometallics, 2002, pp. 3973-3978, vol. 21.

Kornev, A. N. et al., "Tris(Trimethylsilyl)Siloxides of Gadolinium and Lanthanum: Synthesis, Structure and Some Properties", Journal of Organometallic Chemistry, 1999, pp. 113-121, vol. 587.

Covert, J.K. et al., "Carbon-oxygen and related R-X bond cleavages mediated by (silox)3Ti and other Group 4 derivatives ( silox = tBu3SiO)", Inorganic Chimica Acta 263 ( 1997), pp. 263-278.

Hoppe, S.M. et al., Synthesis and characterization of novel metal tris(trimethylsilyl)silanol precursors for production of siloxide-based nanomaterials, Abstracts of Papers, 242nd ACS National Meeting & Exposition, Denver, CO, United States, Aug. 28-Sep. 1, 2011 (2011), CHED-198.

Hoppe, S.M. et al., Synthesis and characterization of novel metal tris(trimethylsilyl)silanol precursors for production of siloxide-based nanomaterials, poster, 242nd ACS National Meeting & Exposition, Denver, CO, United States, Aug. 28-Sep. 1, 2011 (2011), CHED-198.

SINGLE-SOURCE SYNTHESIS OF CERAMIC OXIDE NANOPARTICLES

CROSS-REFERENCE TO RELATED APPLICATION

This application is a continuation-in-part of U.S. application Ser. No. 15/336,296, filed Oct. 27, 2016, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to ceramic nanoparticles and, in particular, to the single-source synthesis of ceramic oxide nanoparticles, including core/shell ceramic oxide nanoparticles.

BACKGROUND OF THE INVENTION

Metal silica-based ($MSiO_x$) materials have found utility in scintillator applications due to their intense luminescent response upon exposure to radiation sources. See H. Retot et al., *J. Phys. D.—Appl. Phys.* 44, 235101 (2011); E. Mihokova et al., *Opt. Mater.* 34, 872 (2012); D. Niznansky et al., *IOP Conf. Series: Mater Sci Eng* 18, 102020 (2011); P. A. Williams et al., *J. Mater. Chem.* 12, 165 (2002); and E. Bescher et al., *J. Sol-Gel Sci. Technol.* 19, 325 (2000). When these materials are doped with lanthanide (Ln) cations, the resultant $MSiO_x$:Ln (i.e., M=barium, bismuth, rare earths) are particularly sensitive and luminescent. See Y. Eagleman et al., *IEEE Trans. Nucl. Sci.* 59, 479 (2012); N. Akchurin et al., *Nucl. Inst. Meth. Phys. Res. Sect A.—Accel., Spect. Detct. Assoc. Eq.* 640, 91 (2011); H. Jiang et al., *J. Ceramic Proc. Res.* 12, S179 (2011); D. Ananias et al., *J. Alloy Cmpds.* 374, 219 (2004); C. W. E. van Eijk et al., *Spect. Detct. Assoc. Eq.* 348, 546 (1994); L. Pidol et al., In *Resh. Trends Contmp. Mat. Sci. Book Ser. Materials Science Forum*, 8th Conf Yugoslav-Mater. Res. Soc., Herceg Novi, Montenegro, 2007, pp 371-376; X. Y. Sun et al., *Int. J. Mater. Res.* 102, 104 (2011). In addition, a number of naturally occurring fluorescent $MSiO_x$ ceramics demonstrate bright emissions, such as zircon ($ZrSiO_4$), benitoite ($BaTiSi_3O_9$), and baghdadite ($Ca_3(Zr,Ti)Si_2O_9$).

However, a need remains for a single-source method to synthesize Ln-doped group 4-5 silicate nanomaterials for scintillator and other applications.

SUMMARY OF THE INVENTION

The present invention is directed to a method to synthesize a metal siloxide precursor, comprising reacting tris(trimethylsilyl)silanol ligand (H-SST) with a Group 4 or 5 metal alkoxide in a solvent to form an SST-modified metal alkoxide precursor. The Group 4 metal can comprise Ti, Zr, or Hf, and the Group 5 metal can comprise V, Nb, or Ta. The alkoxide can comprise $OCH_2CH_3$, $OCHMe_2$, or $OCMe_3$, or $OCH_2CMe_3$ and the solvent can comprise toluene or pyridine. For example, the SST-modified metal siloxide precursor can comprise $[Ti(SST)_2(OR)_2]$, ( wherein OR=$OPr^i$, $OBu^t$, or ONep; $[Ti(SST)_3(OBu^n)]$; $[Zr(SST)_2(OBu^t)_2(py)]$; $[Zr(SST)_3(OR)]$, wherein OR=$OBu^t$ or ONep; $[Hf(SST)_2(OBu^t)_2]$; $[Hf(SST)_2(ONep)_2(py)_n]$, wherein n=1 or 2; $[V(SST)_3(py)_2]$; $[Nb(SST)_3(OEt)_2]$; $[Nb(O)(SST)_3(py)]$; $2[H][(Nb(\mu-O)_2(SST))_6(\mu_6-O)]$; $[Nb_8O_{10}(OEt)_{18}(SST)_2 \cdot \frac{1}{5}Na_2O]$; $[Ta(SST)(\mu-OEt)(OEt)_3]_2$; or $[Ta(SST)_3(OEt)_2]$. The invention can further comprise thermally processing the SST-modified metal siloxide precursor to form a ceramic oxide nanoparticle. The ceramic oxide nanoparticle can comprise a core-shell nanoparticle. The core-shell nanoparticle can comprise a silicate core and a metal oxide shell, such as $ZrO_2$. Alternatively, the core-shell nanoparticle can comprise a metal oxide core, such as $HfO_2$, and a silicate shell.

The majority of these complexes were isolated as monomers but one dimer was also observed. The reduced nuclearity of the $[M(SST)_n(OR)_{x-n}]$ compounds observed for these metals is believed to be due to the steric bulk of the SST, which limits the substitution to n=2 for the group 4 and n=3 for group 5 cations. The lone exception is $[Ti(SST)_3(OBu^n)]$, which possesses the reduced steric bulk of the straight chain $Bu^n$. The low substitution (n=1) of SST noted for $[Ta(SST)(\mu-OEt)(OEt)_3]_2$ retains the standard dinuclear geometry of $[Ta(OR)_5]$ complexes. The solubility of the ceramic in glass coupled with the time and temperature of heating schedules dictates at least some of the final core@shell arrangements.

BRIEF DESCRIPTION OF THE DRAWINGS

The detailed description will refer to the following drawings, wherein like elements are referred to by like numbers.

FIG. 10(a) is a structure plot of $[Hf(SST)_2(ONep)_2(py)_t]$, referred to herein as compound 10a.

DETAILED DESCRIPTION OF THE INVENTION

Figure 1:
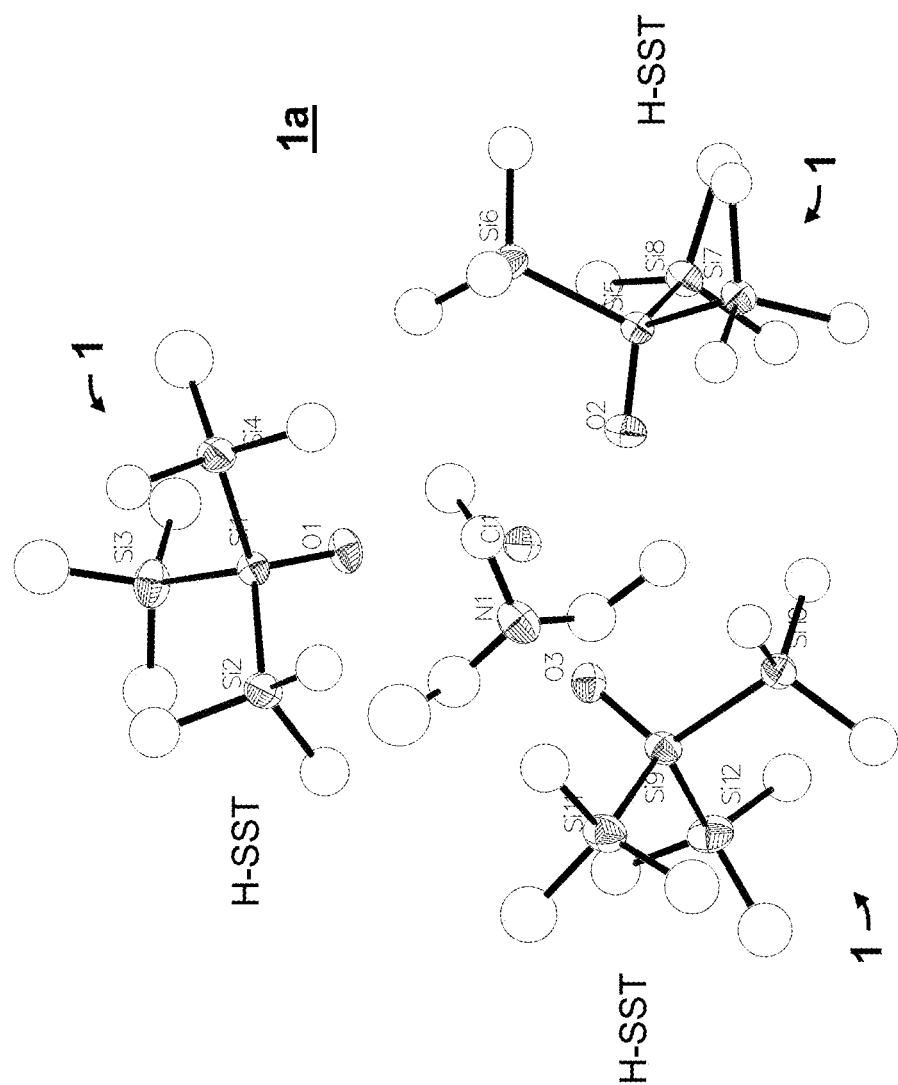
FIG. 1 is a schematic representation of the structure adopted for the salt 1a with the inclusion of $HCl.N(Et)_3$ and three tris-(trimethylsilyl)silanol (H-SST, 1) ligands.

The production of metal silicates (MSiO$_x$) has been widely investigated using a variety of synthetic pathways. For routes that employ metal alkoxides ([M(OR)$_x$]), the MSiO$_x$ products are reportedly generated from the reaction of the desired metal precursor with a Si(OR)$_4$ or by employing metal siloxide precursors [M(OSiR$_3$)$_x$]. See S. Lee et al., *J. Mater. Chem.* 19, 6857 (2009); S. Tanriverdi et al., *Mater Sci-Poland* 25, 957 (2007); S. Katayama et al., *J. Eur. Ceram. Soc.* 24, 421 (2004); S. M. Jones, *J. Non-Cryst. Sol.* 291, 206 (2001); T. Mabuchi and T. Fugii, *Bull. Chem. Soc. Jpn.* 66, 2174 (1993); K. Samedov et al., *ChemPlusChem* 77, 663 (2012); M. Mehring et al., *Eur. J. Inorg. Chem.*, 4891 (2005); W.-K. Kim et al., *J. Vac. Sci. Tech. A (Vac. Surf. Films)* 22, 1285 (2004); and C. C. Trapalis et al., *Nanostructured MeSiO(2) (Me=Ag, Cu) coatings with antibacterial activity*, Springer: Dordrecht, Netherlands, 2003. However, these approaches have met with varying degrees of success in converting to the desired MSiO$_x$. In particular, the inventors have found that, after processing the [M(OSiR$_3$)$_x$] precursors, the phase separated nano-oxides were isolated instead of the desired mixed MSiO$_x$.

Therefore, tris(trimethylsilyl)silanol (HOSi(Si(CH$_3$)$_3$)$_3$ or H-SST)-modified [M(OR)$_4$] was investigated as a potential single-source precursor to MSiO$_x$. The H-SST ligand is of interest due to the different internal bond strengths, where the Si—Si bond strength (326.8 kJ/mol) is less than the Si—C (435 kJ/mol) and much less than the Si—O (798.7 kJ/mol) bonds. Further, upon complexation to a group 4 metal [Ti—O (661.9 kJ/mol), Zr—O (759.8 kJ/mol), Hf—O (794.1 kJ/mol), V—O (644 kJ/mol), Nb—O (753 kJ/mol), Ta—O (805.0 kJ/mol)], the Si—Si bond still remains the weakest link. See *Handbook of Chemistry and Physics, 81st Edition CRC Press ISBN 0-8493-0481-4*. CRC Press: Boca Raton, Fla. (1980). Therefore, it was anticipated that with proper processing of a '[M(SST)$_n$(OR)$_{x-n}$]' compound, the oxide could be avoided and the desired MSiO$_x$ generated.

A search of the structure literature indicates that there are only a handful of SST-ligated metal complexes that have been crystallographically characterized. See A. N. Kornev, *Russ. Chem. Rev.* 73, 1065 (2004); T. A. Chesnokova et al., *J. Organomet. Chem.* 642, 20 (2002); A. N. Kornev et al., *J. Organomet. Chem.* 547, 113 (1997); A. N. Kornev et al., *Dokl. Akad. Nauk. SSR (Russ.) (Proc. Nat. Acad. Sci. USSR)* 369, 203 (1999); and Z. Wu et al., *Organometallics* 21, 3973 (2002). Since there were no structure reports published for SST derivatives of the group 4 or 5 metals, the synthesis of a series of SST-ligated [M(OR)$_x$] was undertaken to develop a single-source precursor for production of MSiO$_x$ nanoparticles. The H-SST ligand was synthesized following slightly modified literature procedures to isolate the pure oil. See H. Gilman and R. L. Harrell, *J. Organomet. Chem.* 5, 199 (1966); A. N. Kornev et al., *Russ. Chem. Bull.* 44, 1107 (1995); and B. H. Boo et al., *J. Organomet. Chem.* 436, 1 (1992). The group 4 and 5 [M(OR)$_x$] selected for investigation used the commercially available OEt, OPr$^i$ or OBu, as well as the synthesized ONep alkoxy compounds. The coordination behavior of the pure H-SST with a series of group 4 and 5 [M(OR)$_x$] at room temperature was undertaken following eq 1.

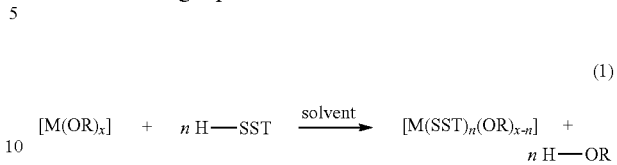

As described below, the products isolated from eq 1 were crystallographically characterized as: [Ti(SST)$_2$(OR)$_2$] (OR=OPr$^i$(2), OBu$^t$ (3), ONep (4)), [Ti(SST)$_3$(OBu")] (5), [Zr(SST)$_2$(OBu$^t$)$_2$(py)] (6), [Zr(SST)$_3$(OR)] (OR=OBu$^t$ (7) ONep (8)), [Hf(SST)$_2$(OBu$^t$)$_2$] (9), [Hf(SST)$_2$(ONep)$_2$(py)$_n$] (n=1 (10a); n=2 (10b)), [V(SST)$_3$(py)$_2$] (11), [Nb(SST)$_3$ (OEt)$_2$] (12), [Nb(O)(SST)$_3$(py)] (13), 2[H][(Nb(µ-O)$_2$ (SST))$_6$(µ$_6$-O)] (14), [Nb$_8$O$_{10}$(OEt)$_{18}$(SST)$_2$·⅓Na$_2$O] (15), [Ta(SST)(µ-OEt)(OEt)$_3$]$_2$ (16), and [Ta(SST)$_3$(OEt)$_2$] (17) where OEt=OCH$_2$CH$_3$, OPr$^i$=OCH(CH$_3$)$_2$, OBu$^t$= OC(CH$_3$)$_3$, OBu"=O(CH$_2$)$_3$CH$_3$, ONep=OCH$_2$C(CH$_3$)$_3$, and py=pyridine. Based on the thermal analysis of the isolated powders, attempts were made to convert these precursors into silicate-based group 4 and 5 oxide materials. However, instead of the expected MSiO$_x$ species, unusual core-shell architectures were observed, as is described below.

Synthesis

The H-SST ligand was synthesized according to the literature preparative routes with minor modifications noted below. See H. Gilman and R. L. Harrell, *J. Organomet. Chem.* 5, 199 (1966); A. N. Kornev et al., *Russ. Chem. Bull.* 44, 1107 (1995); and B. H. Boo et al., *J. Organomet. Chem.* 436, 1 (1992). As an example, H—Si(Si(CH$_3$)$_3$)$_3$ (20.0 g, 80.4 mmol) was stirred with heating in CHCl$_3$:CCl$_4$ (100:25 mL) at reflux temperatures for 4 h, allowed to cool to room temperature, and dried in vacuo. The resulting yellow powder was re-dissolved in hexanes, had a mixture of water and N(Et)3 (75:50 mL) added, and stirred for an additional 24 h. The organic fraction was separated from the aqueous, dried over NaSO$_4$ (~10 g), filtered, vacuum distilled to an oil, and stored over dried molecular sieves for 24 h prior to use. The yield of H-SST ligand was 96.9% (25.8 g). From one incompletely washed reaction mixture, crystals were isolated as 3(H-SST).HN(CH$_2$CH$_3$)$_3^+$.Cl$^-$. FIG. 1 shows the structure adopted for the salt 1a with the inclusion of HCl.N(Et)$_3$ and three H-SST ligands 1 (The C atoms are not labeled in these figures. H atoms are omitted for clarity).

To generate the [M(SST)$_n$(OR)$_{x-n}$] precursor, stoichiometric amounts of H-SST were added to a stirring solution of the appropriate M(OR)$_x$ dissolved in the desired solvent. The M(OR)$_x$ reactants were synthesized according to literature procedures. See T. J. Boyle et al., *Inorg. Chem.* 36, 3293 (1997); and T. J. Boyle et al., *Inorg. Chem.* 49, 10798 (2010). After 12 h, the reaction was set aside to allow the volatile components to slowly evaporate until crystals grew. After this time, the mother liquor was decanted off, crystals removed for single crystal analysis and the remaining crystals dried in vacuo and used for all additional analyses. Yields were not optimized. Examples of the synthesis of exemplary precursors are described below.

Figure 2:
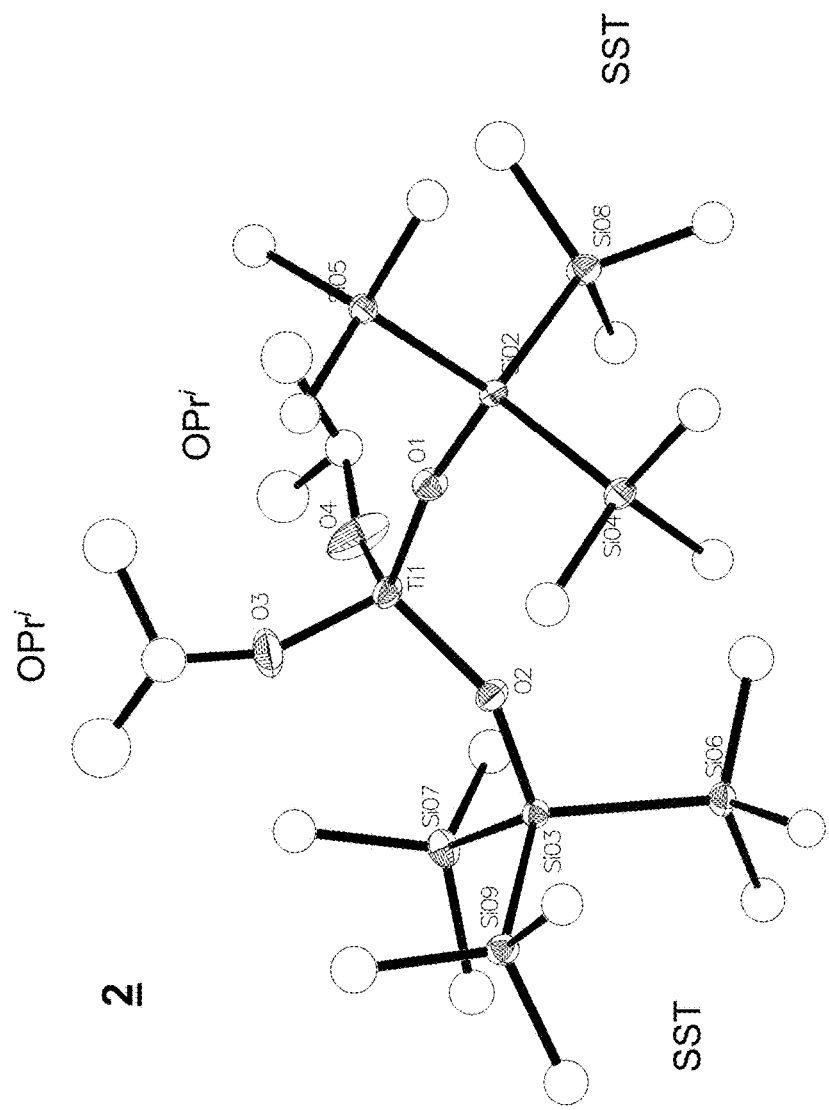
FIG. 2 is a structure plot of $[Ti(SST)_2(OPr^i)_2]$, referred to herein as compound 2.

[Ti(SST)$_2$(OPr$^i$)$_2$] was synthesized by reacting titanium iso-propoxide [Ti(OPr$^i$)$_4$] (0.269 g, 0.946 mmol) with H-SST (0.500 g, 1.89 mmol) in ~10 mL of toluene. The yield was 73.7% (0.484 g). A structure plot of [Ti(SST)$_2$(OPr$^i$)$_2$] (2) is shown in FIG. 2.

Figure 3:
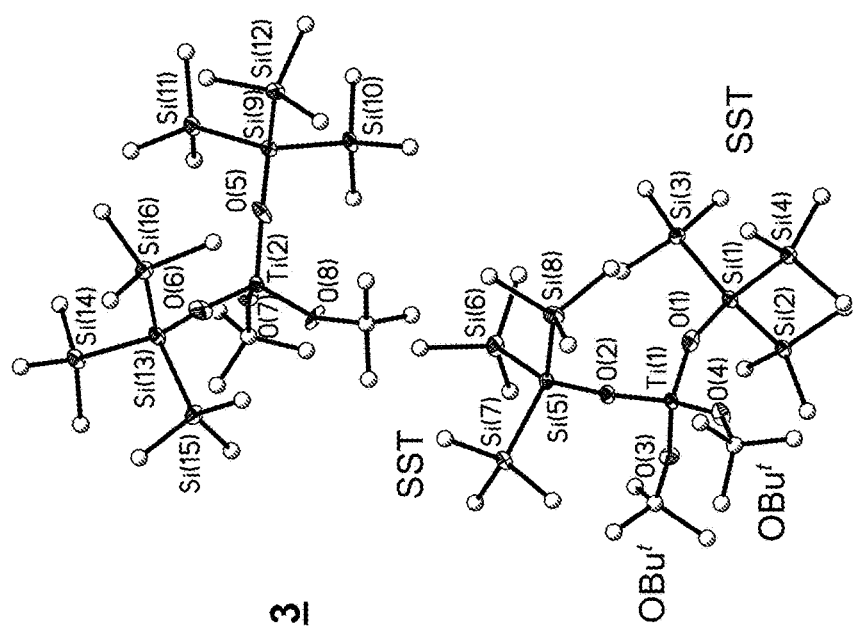
FIG. 3 is a structure plot of $[Ti(SST)_2(OBu^t)_2]$, referred to herein as compound 3.

[Ti(SST)$_2$(OBu$^t$)$_2$] was synthesized by reacting titanium tert-butoxide [Ti(OBu$^t$)$_4$] (0.322 g, 0.946 mmol) with H-SST (0.500 g, 1.89 mmol) in ~10 mL of toluene. The yield was 79.4% (0.543 g). A structure plot of [Ti(SST)$_2$(OBu$^t$)$_2$] (3) is shown in FIG. 3.

Figure 4:
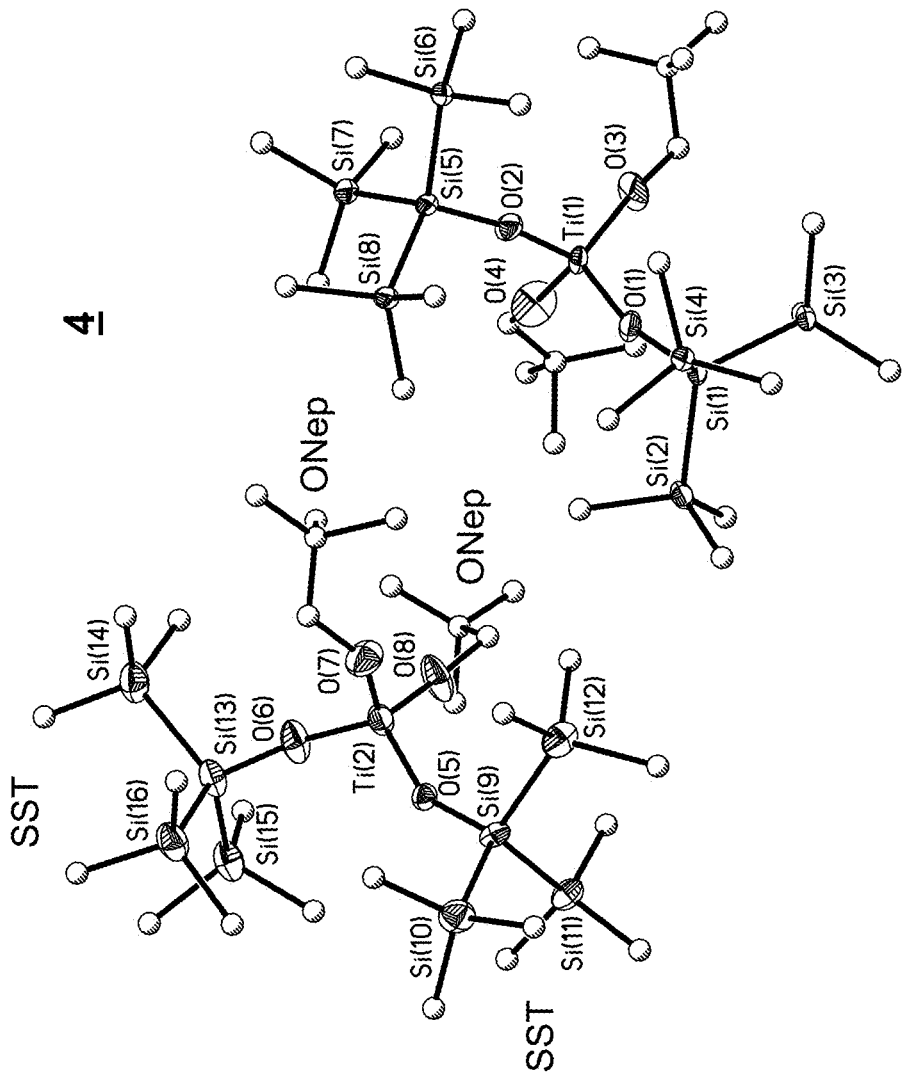
FIG. 4 is a structure plot of $[Ti(SST)_2(ONep)_2]$, referred to herein as compound 4.

[Ti(SST)$_2$(ONep)$_2$] was synthesized by reacting the titanium ONep derivative [Ti(ONep)$_4$] (0.374 g, 0.946 mmol) with H-SST (0.500 g, 1.89 mmol) in ~10 mL of toluene. The yield was 74.6% (0.530 g). A structure plot of [Ti(SST)$_2$(ONep)$_2$] (4) is shown in FIG. 4.

Figure 5:
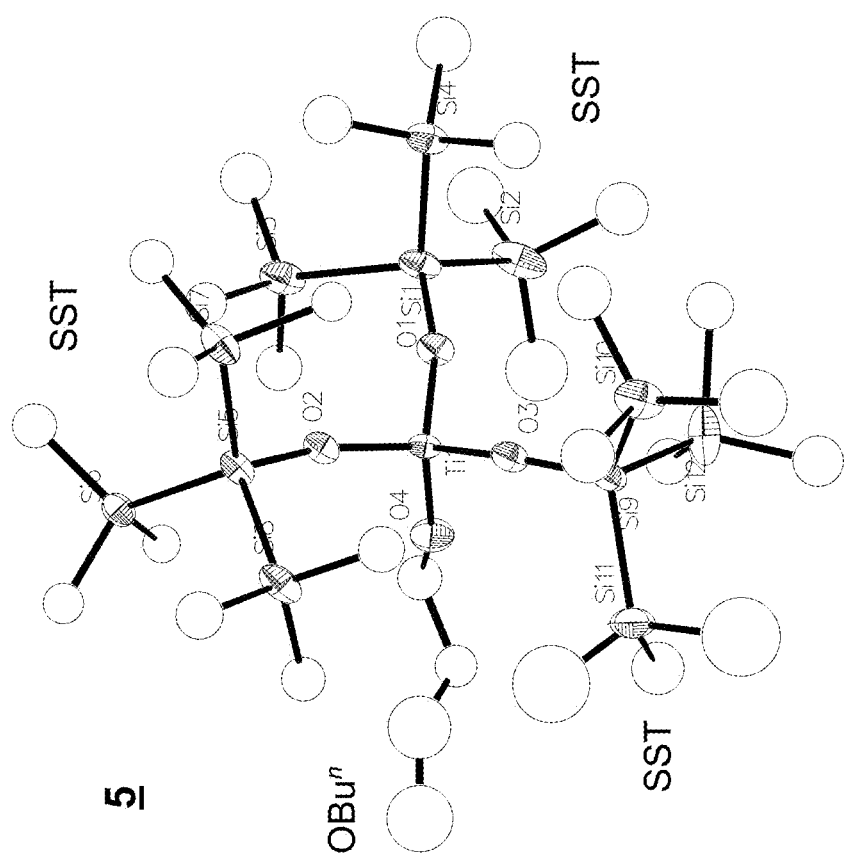
FIG. 5 is a structure plot of $[Ti(SST)_3(OBu^n)]$, referred to herein as compound 5.

[Ti(SST)$_3$(OBu$^n$)] was synthesized by reacting titanium n-butoxide [Ti(OBu$^n$)$_4$] (0.214 g, 0.630 mmol) with H-SST (0.500 g, 1.89 mmol) in ~10 mL of toluene. The yield was 75.0% (0.439 g). A structure plot of [Ti(SST)$_3$(OBu$^n$)] (5) is shown in FIG. 5.

Figure 6:
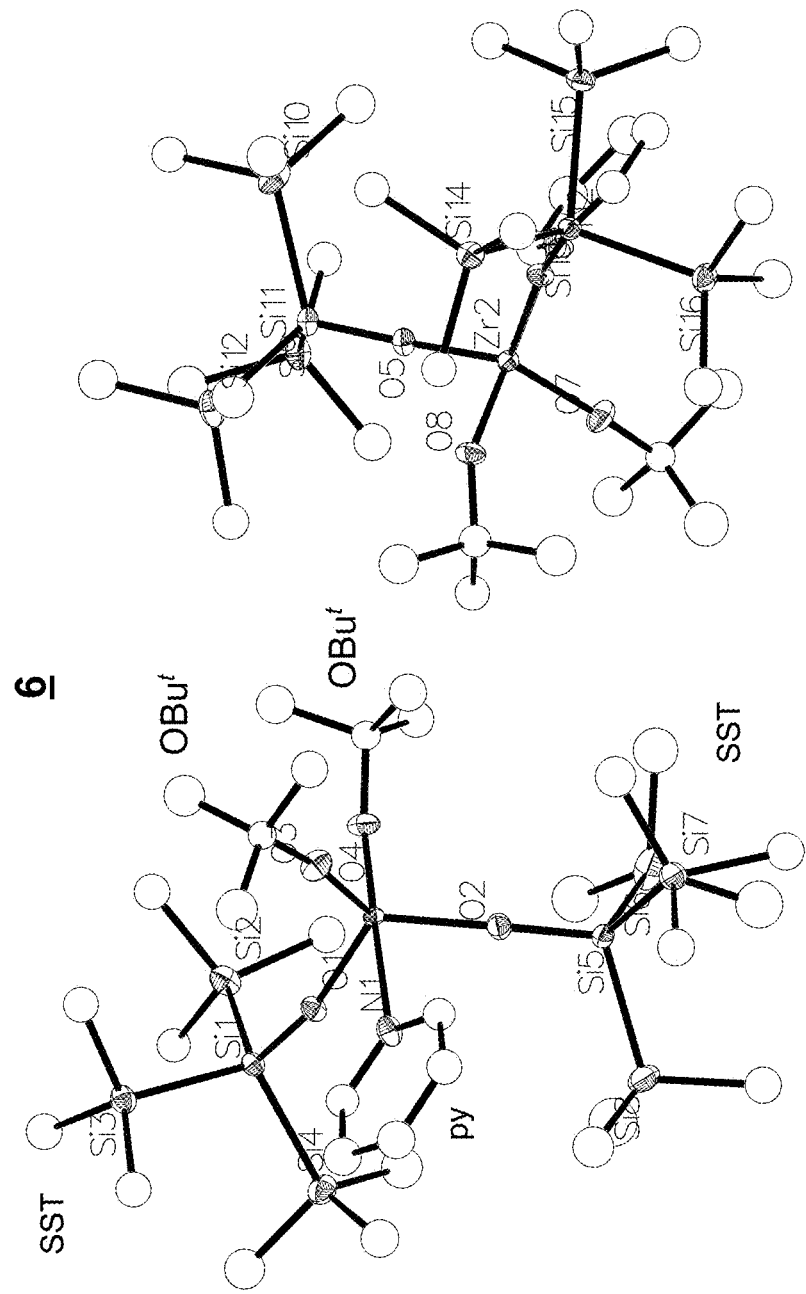
FIG. 6 is a structure plot of $[Zr(SST)_2(OBu^t)_2(py)]$, referred to herein as compound 6.

[Zr(SST)$_2$(OBu$^t$)$_2$(py)] was synthesized by reacting zirconium tert-butoxide [Zr(OBu$^t$)$_4$] (0.364 g, 0.945 mmol) with H-SST (0.500 g, 1.89 mmol) in ~10 mL of pyridine. The yield was 66.6% (0.533 g). A structure plot of [Zr(SST)$_2$(OBu$^t$)$_2$(py)] (6) is shown in FIG. 6.

Figure 7:
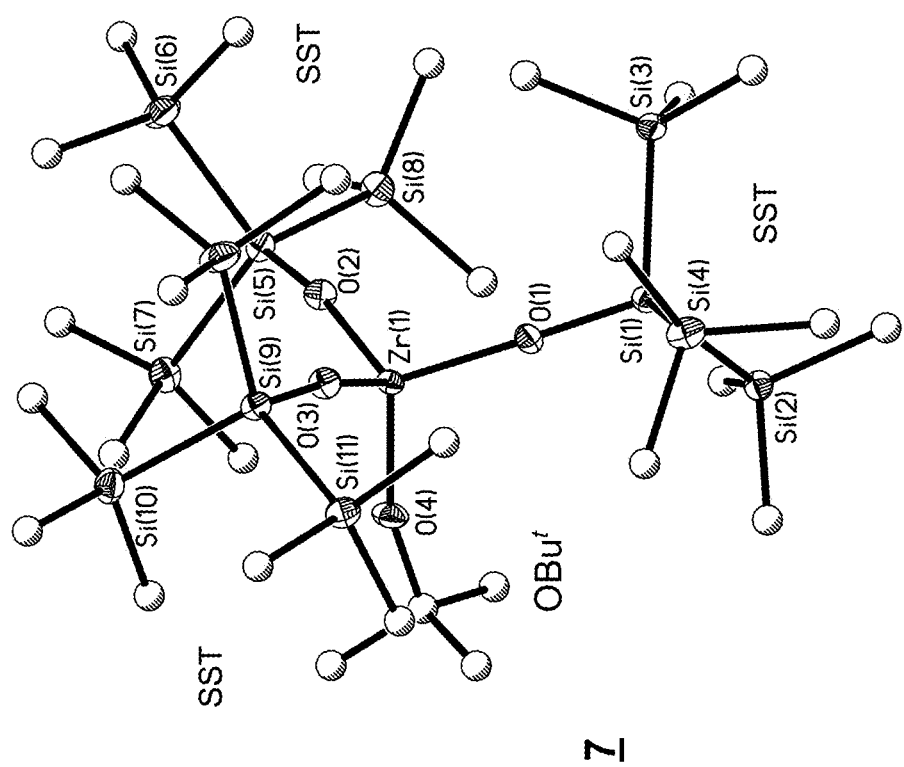
FIG. 7 is a structure plot of $[Zr(SST)_3(OBu^t)]$, referred to herein as compound 7.

[Zr(SST)$_3$(OBu$^t$)] was synthesized by reacting zirconium tert-butoxide [Zr(OBu$^t$)$_4$] (0.25 g, 0.653 mmol) with H-SST (0.517 g, 1.96 mmol) in ~10 mL of toluene. The yield was 83.5% (0.521 g). A structure plot of [Zr(SST)$_3$(OBu$^t$)] (7) is shown in FIG. 7.

Figure 8:
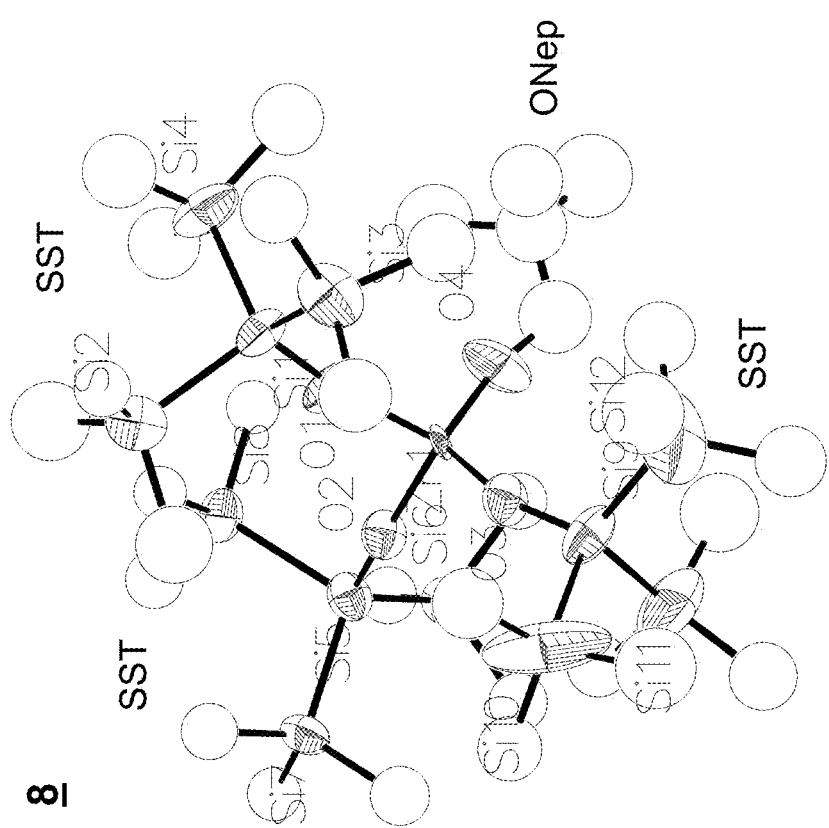
FIG. 8 is a structure plot of $[Zr(SST)_3(ONep)]$, referred to herein as compound 8.

[Zr(SST)$_3$(ONep)] was synthesized by reacting the zirconium ONep derivative [Zr(ONep)$_4$]$_2$ (0.277 g, 0.630 mmol) with H-SST (0.500 g, 1.89 mmol) in ~10 mL of toluene. The yield was 77.0% (0.472 g). A structure plot of [Zr(SST)$_3$(ONep)] (8) is shown in FIG. 8.

Figure 9:
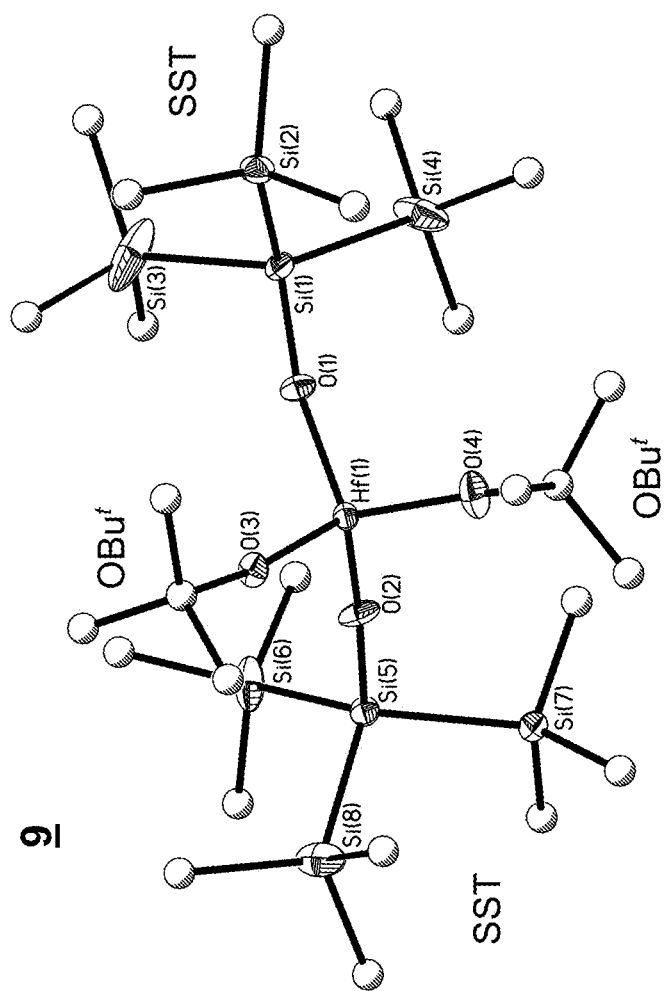
FIG. 9 is a structure plot of $[Hf(SST)_2(OBu^t)_2]$, referred to herein as compound 9.

[Hf(SST)$_2$(OBu$^t$)$_2$] was synthesized by reacting hafnium tert-butoxide [Hf(OBu$^t$)$_4$] (0.446 g, 0.945 mmol) with H-SST (0.500 g, 1.89 mmol) in ~10 mL of pyridine. The yield was 77.5% (0.682 g). A structure plot of [Hf(SST)$_2$(OBu$^t$)$_2$] (9) is shown in FIG. 9.

Figure 10A:
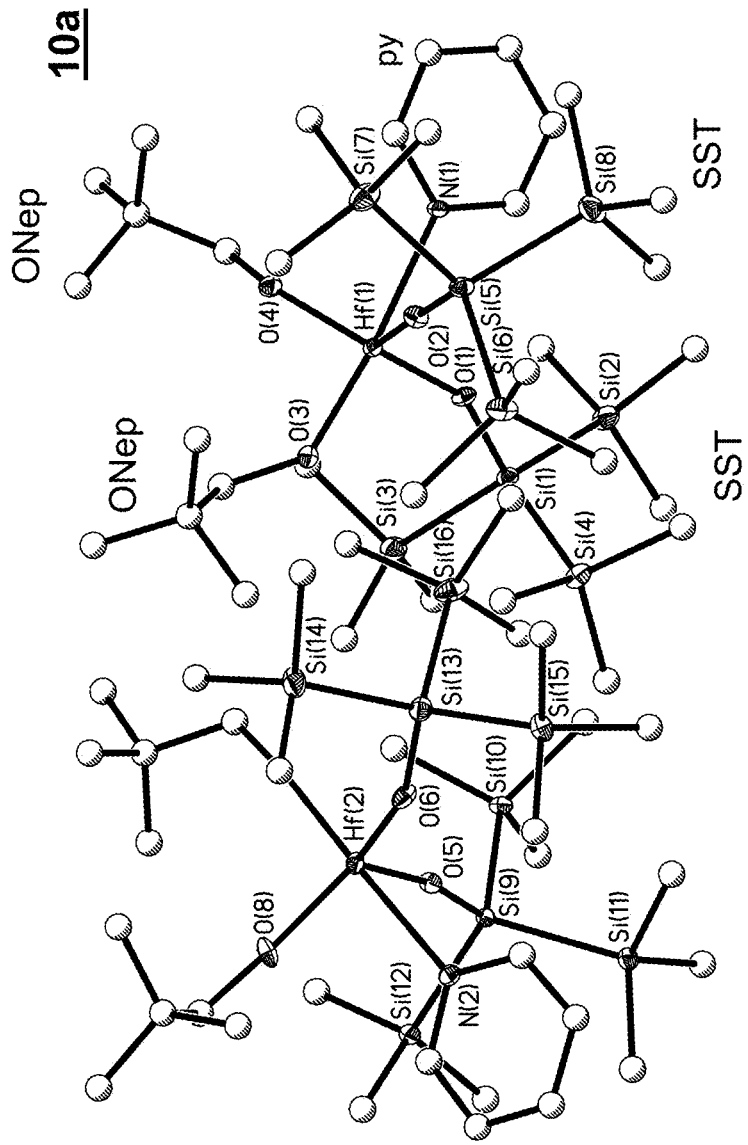
Figure 10B:
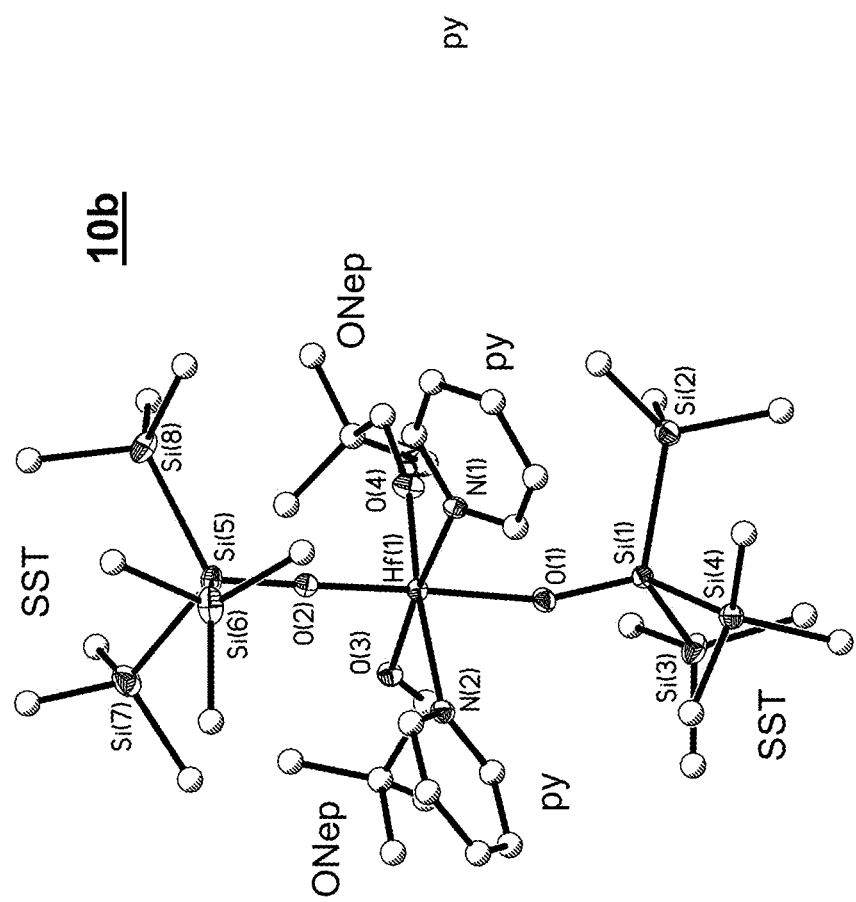
FIG. 10(b) is a structure plot of $[Hf(SST)_2(ONep)_2(py)_2]$, referred to herein as compound 10b.

[Hf(SST)$_2$(ONep)$_2$(py)$_n$] (n=1 (10a); n=2 (10b)) was synthesized by reacting the hafnium ONep derivative [Hf(ONep)$_4$] (0.535 g, 0.945 mmol) with H-SST (0.500 g, 1.89 mmol) in ~10 mL of pyridine. The yield was 75.8% (0.687 g). A structure plot of [Hf(SST)$_2$(ONep)$_2$(py)$_1$] (10a) is shown in FIG. 10a. A structure plot of [Hf(SST)$_2$(ONep)$_2$(py)$_2$] (10b) is shown in FIG. 10b.

Figure 11:
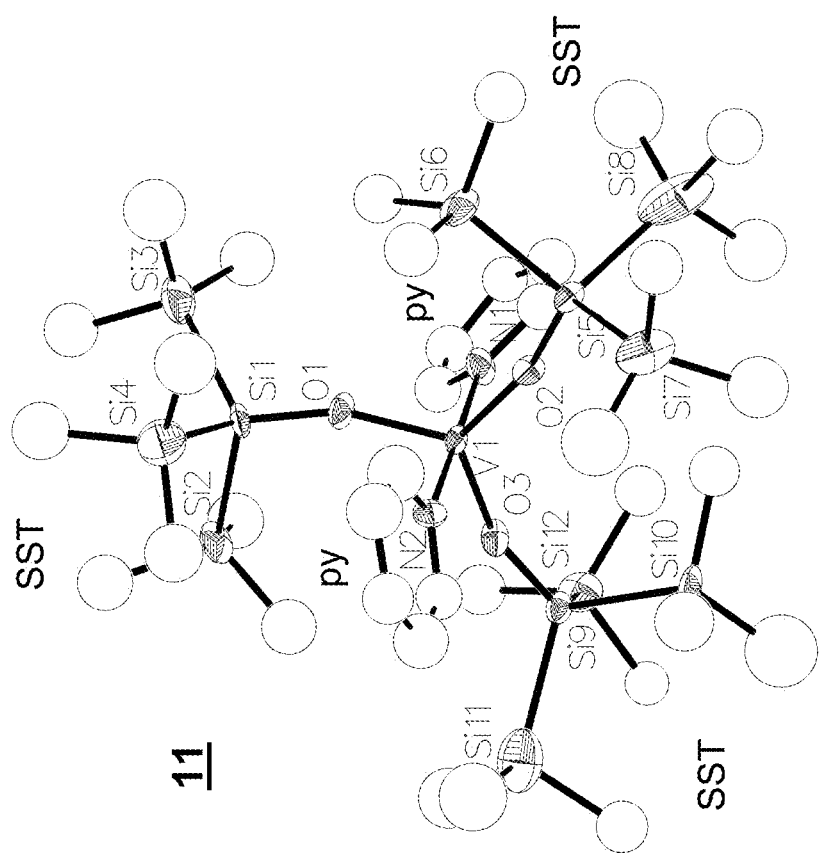
FIG. 11 is a structure plot of $[V(SST)_3(py)_2]$, referred to herein as compound 11.

[V(SST)$_3$(py)$_2$] was synthesized by reacting vanadium oxo chloride [V(O)(Cl)$_3$] (2.00 g, 11.5 mmol) with H-SST (9.25 g, 37.2 mmol) in 200 mL of toluene, 3 mL of trimethylamine, and pyridine (2 mL). This mixture was heated to 60° C., filtered, concentrated, and OEt$_2$ (120 mL) was added. The reaction mixture was allowed to slowly evaporate until crystals formed. The yield was 72.7% (6.41 g). A structure plot of [V(SST)$_3$(py)$_2$] (11) is shown in FIG. 11.

Figure 12:
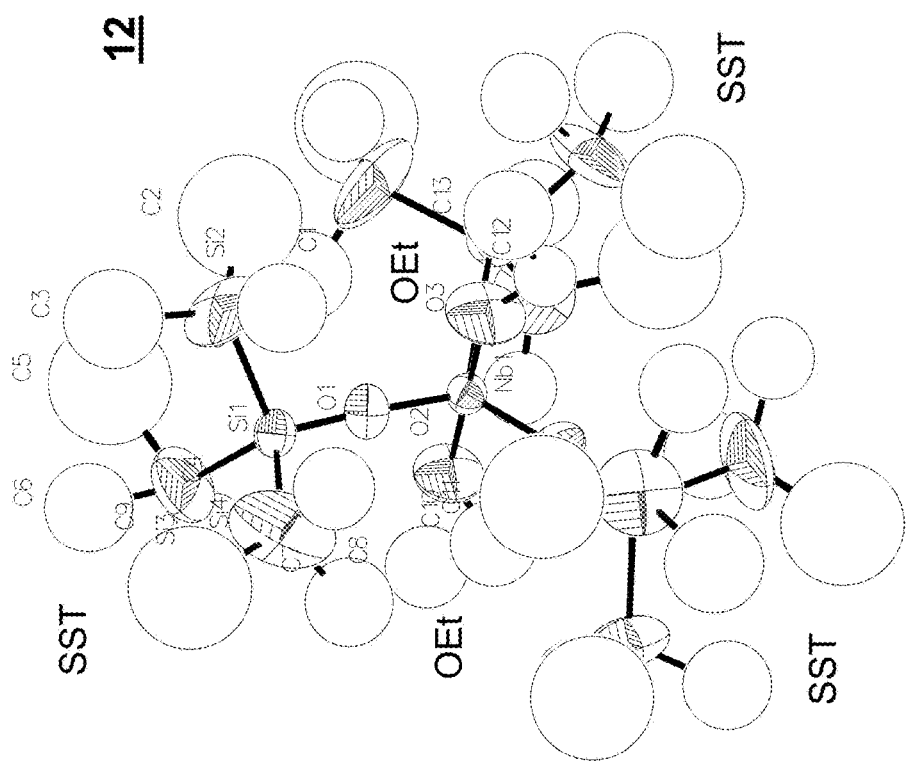
FIG. 12 is a structure plot of $[Nb(SST)_3(OEt)_2]$, referred to herein as compound 12.

[Nb(SST)$_3$(OEt)$_2$] was synthesized by reacting niobium ethoxide [Nb(OEt)$_5$] (0.100 g, 0.314 mmol) with H-SST (0.250 g, 0.942 mmol) in ~10 mL of toluene. The yield was 90.2% (0.276 g). A structure plot of [Nb(SST)$_3$(OEt)$_2$] (12) is shown in FIG. 12.

Figure 13:
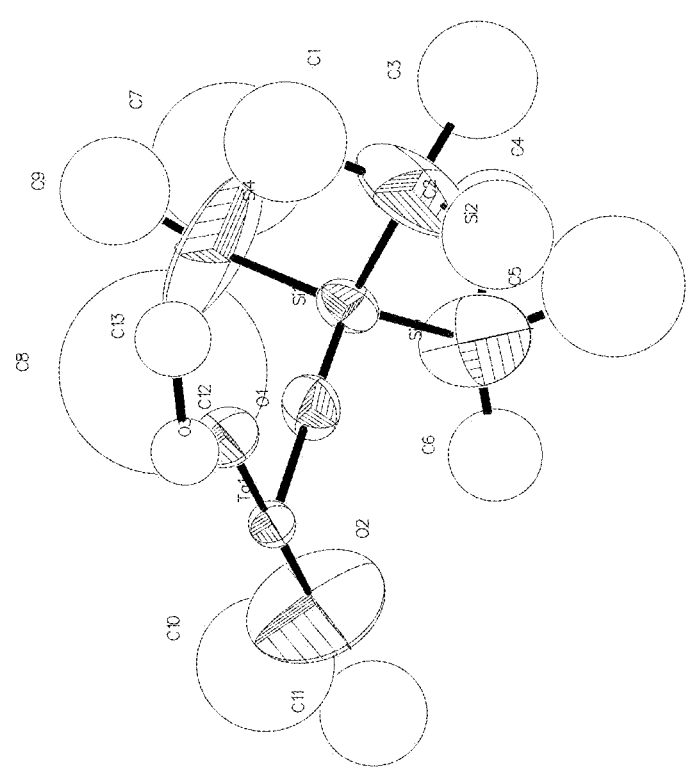
FIG. 13 is a structure plot of $[(SST)Ta(OEt)_2]$.
Figure 14:
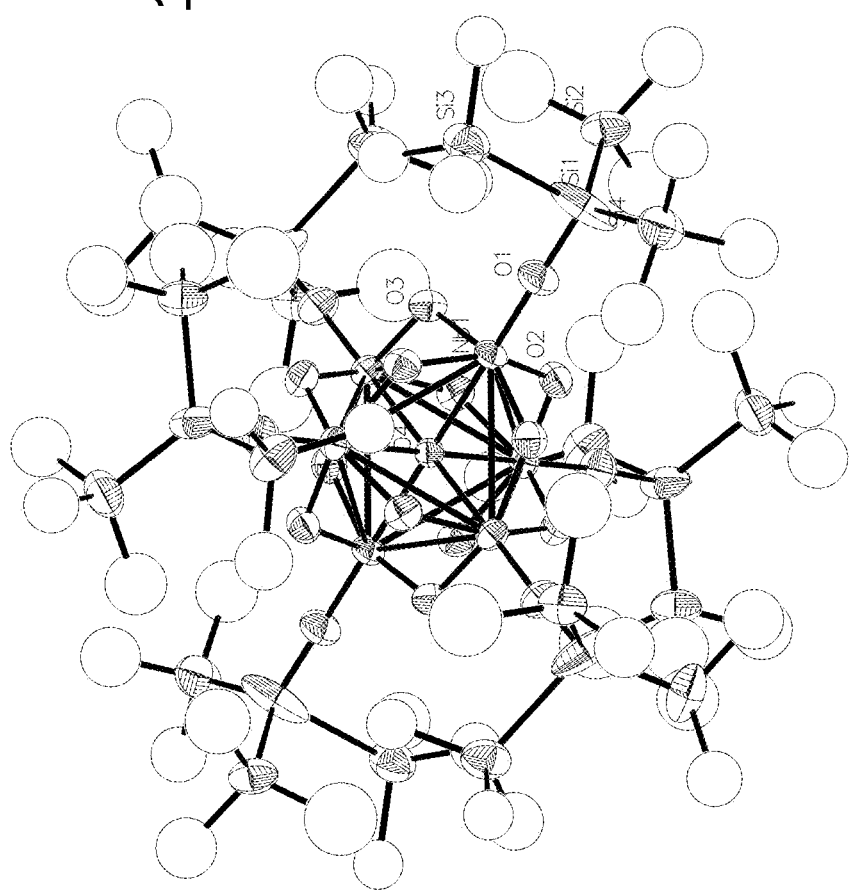
FIG. 14 is a structure plot of $2[H][(Nb(\mu-O)_2(SST))_6(\mu_6-O)]$, referred to herein as compound 14.
Figure 15A:
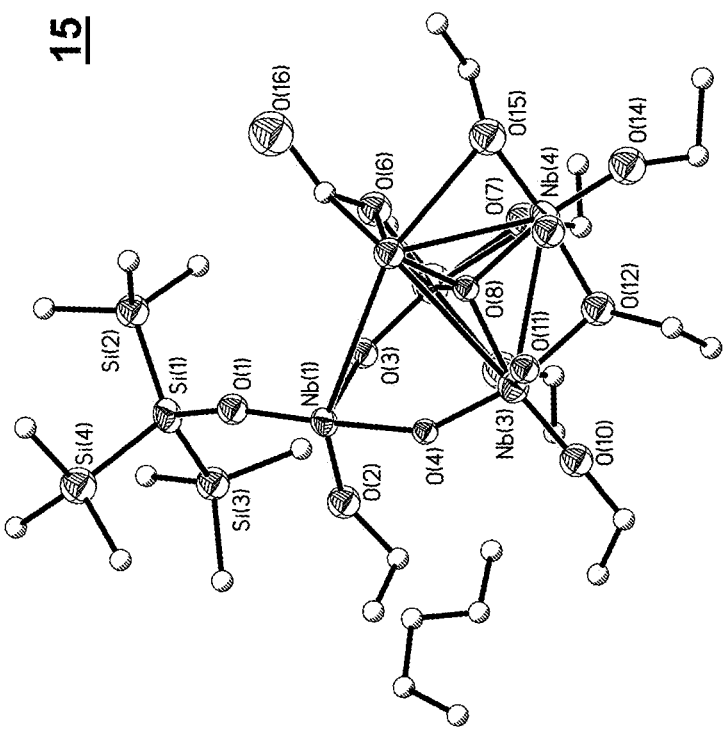
FIG. 15(a) is a structure plot of $[Nb_8O_{10}(OEt)_{18}(SST)_2 \cdot \frac{1}{5}Na_2O]$, referred to herein as compound 15.
Figure 15B:
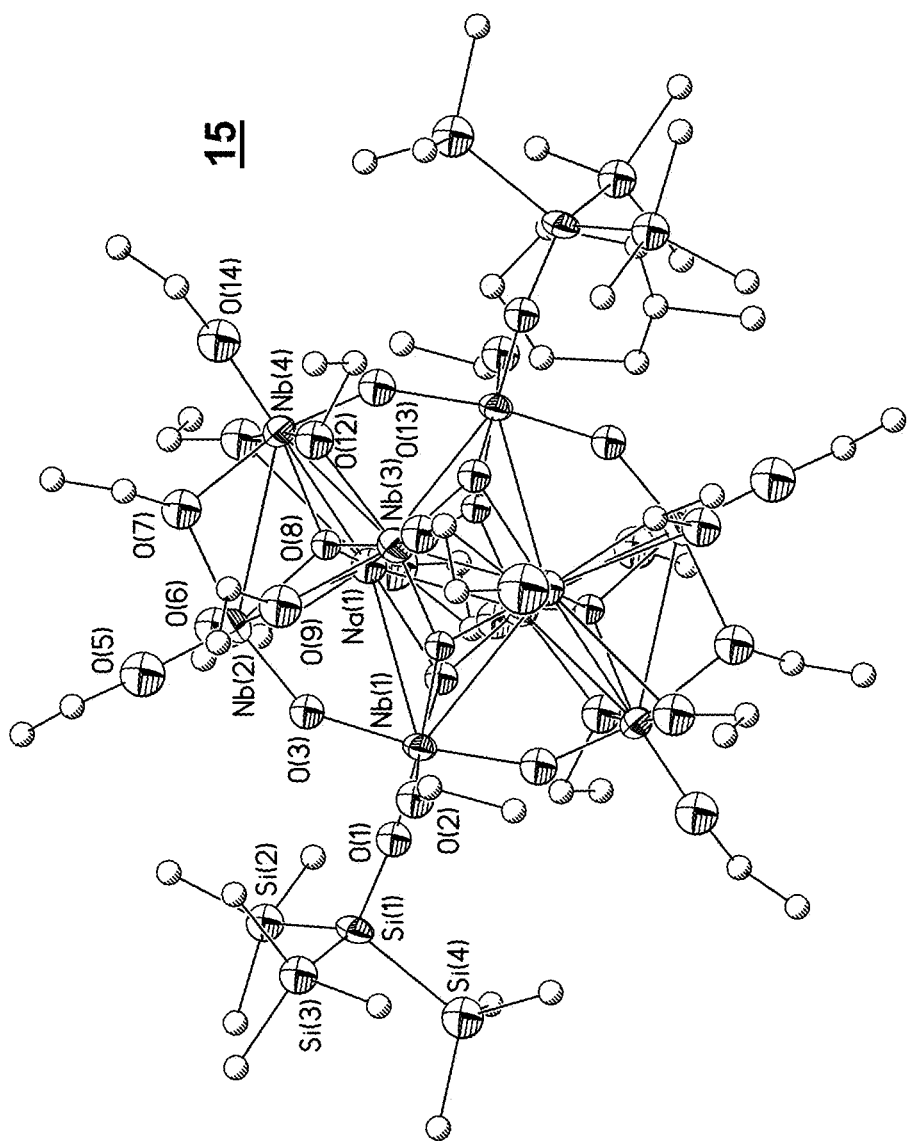
FIG. 15(b) is an expanded view.

[(SST)Ta(OEt)$_2$] was synthesized by reacting tantalum ethoxide [Ta(OEt)$_5$] (0.768g, 1.89 mmol) with H-SST (0.500 g, 1.89 mmol) in ~10 mL of toluene. The yield was 48.1% (0.567 g). A structure plot of [(SST)Ta(OEt)$_2$] is shown in FIG. 13.

[Nb(O)(SST)$_3$(py)] (13) was synthesized by reacting niobium ethoxide [Nb(OEt)$_5$] (0.100 g, 0.314 mmol) with H-SST (0.250 g, 0.942 mmol) in ~10 mL of pyridine.

Figure 16:
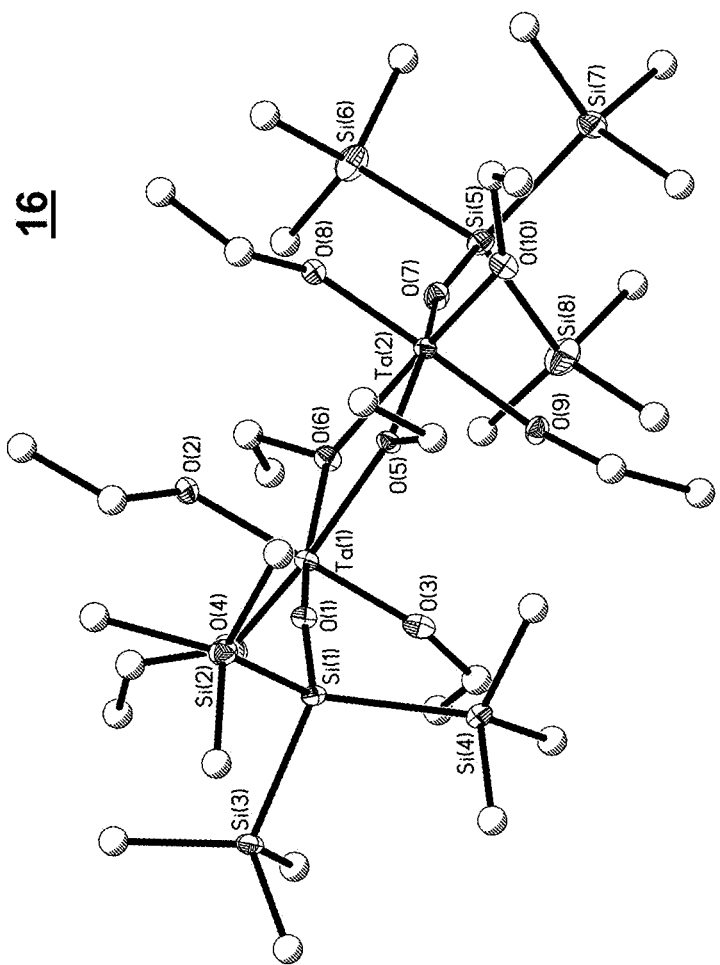
FIG. 16 is a structure plot of $[Ta(SST)(\mu-OEt)(OEt)_3]_2$, referred to herein as compound 16.

[Ta(SST)(μ-OEt)(OEt)$_3$]$_2$ was synthesized by reacting tantalum ethoxide [Ta(OEt)$_5$] (0.770 g, 1.89 mmol) with H-SST (0.500 g, 1.89 mmol) in ~10 mL of toluene. The yield was 48.1% (0.567 g). A structure plot of [Ta(SST)(μ-OEt)(OEt)$_3$]$_2$ (16) is shown in FIG. 16.

Figure 17:
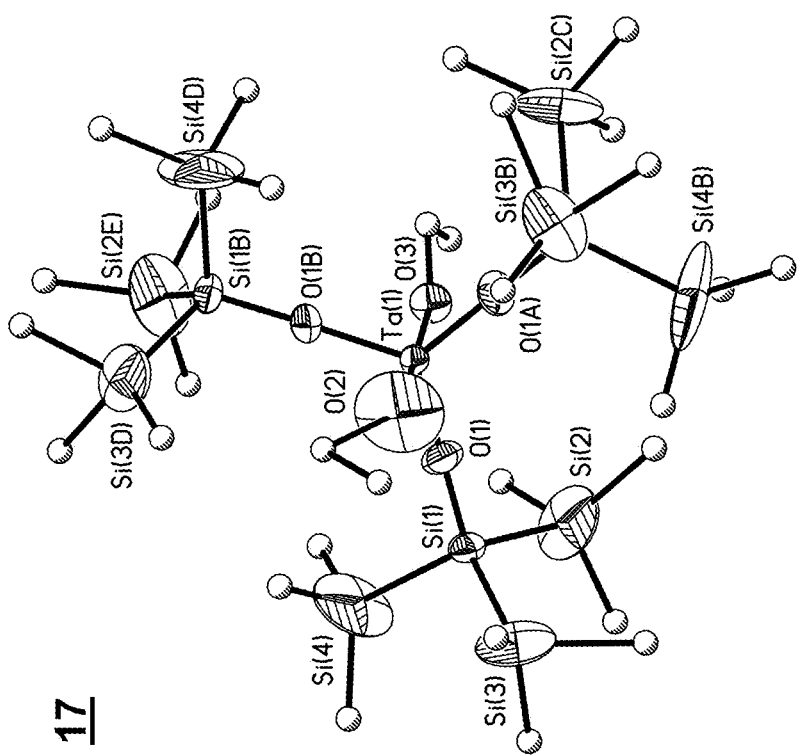
FIG. 17 is a structure plot of $[Ta(SST)_3(OEt)_2]$, referred to herein as compound 17.

[Ta(SST)$_3$(OEt)$_2$] was synthesized by reacting tantalum ethoxide [Ta(OEt)$_5$] (0.256 g, 0.630 mmol) with H-SST (0.500 g, 1.89 mmol) in ~10 mL of toluene. The yield was 87.6% (0.589 g). A structure plot of [Ta(SST)$_3$(OEt)$_2$] (17) is shown in FIG. 17.

Characterization

The products isolated from eq 1 ([M(SST)$_n$(OR)$_{x-n}$] (x=4, 2-10b; x=5, 11-13, 16-17) were characterized using FTIR spectroscopy, single crystal X-ray diffraction, elemental analyses, and NMR spectroscopy. The lack of a rational route to 14 or 15 precluded detailed analytical analyses but their structures are reported for completeness and to aid in identifying potential products from these reactions. Note: when a series of structures are presented (i.e., 1-17), this series will not include compounds 14 and 15. In general, the FTIR data revealed that the H-SST had reacted with the M(OR)$_x$ and successfully replaced several parent alkoxide ligands. The $^1$H NMR data for 1-17 displayed the expected resonances associated with the OR and SST moieties. For all of the samples investigated, two $^{29}$Si NMR resonances were observed: quaternary [Si(Si(CH$_3$)$_3$)$_3$] and the terminal [Si(Si(CH$_3$)$_3$)$_3$]. For the H-SST ligand, a quaternary shift and a terminal shift were observed. Upon binding to the metals, the $^{29}$Si chemical shift of the terminal moiety was not dramatically impacted regardless of the metal. Overall, the quaternary $^{29}$Si shifts appear to be influenced greatly by the metal bound to them but not by the degree of substitution by the SST ligand and is a useful flag for characterizing the different compounds. Single crystal X-ray experiments were undertaken to elucidate the coordination behavior of the SST ligand. FIGS. 1-17 show representative species for the various metals and alkoxides isolated. Table 1 shows the crystallographic data.

Group 4 Derivatives

For the Ti system, compounds 2-4 were isolated as simple, monomeric, di-substituted species. Each metal center was found to adopt a distorted T-4 geometry. FIG. 2 shows the representative structure of 2 for this set of complexes. Switching to the less sterically demanding OBu$^n$ generated a tri-substituted species, 5, as shown in FIG. 5. The structure of 5 was also found to be monomeric with a T-4 coordinated metal center retaining only one of the parent OBu$^n$ ligands. Interestingly, compounds 2-5 were the only products isolated from all attempts to further increase or reduce siloxide coordination.

Altering the alkoxide precursor to the heavier congener, [Zr(OBu$^t$)$_4$] led to the isolation of the solvated monomeric di-siloxide species 6. The presence of a bound py molecule forces a rigorous trigonal bipyramidal geometry (TBPY-5; two molecules per unit cell) and indicates additional coordination sites are accessible around the metal center. Therefore, increased siloxide substitutions were attempted and realized through the isolation of the tri-substituted SST derivatives 7 (OBu$^t$) and 8 (ONep). The metal centers of these complexes were isolated in distorted T-4 geometry.

The [Hf(OR)$_4$] (OR=OBu$^t$ and ONep) derivatives were also investigated and found to produce the monomeric, di-siloxide complex 9 (OBu$^t$). The Hf metal center was solved in a distorted T-4 arrangement using two parent alkoxides and the two SST ligands. In contrast, compound 10a had the dual SST and ONep ligand set along with an additional pyridine solvent molecule bound to Hf metal center. This arrangement resulted in a TBPY-5 geometry. From an identical reaction, another solvated "Hf(ONep)$_2$(SST)$_2$" moiety 10b was crystallographically characterized, but for this molecule, two pyridine solvent molecules were bound to the metal center forcing a distorted octahedral (OC-6) geometry.

Group 5 Derivatives

The SST-modifications of a set of group 5 alkoxides were also explored. Attempts to generate V-SST complexes from the substitution of [V(O)(OR)$_3$] (OR=OEt, OPr$^i$) were undertaken and the partial structure solutions of [V(OPr$^i$)$_2$(SST)$_3$] and [V(O)(SST)$_2$(OEt)] were obtained. An alternative route to V-SST compounds that proved to be reliable was the alcholysis of vanadium oxy chloride [(O)VCl$_3$]. Surprisingly, the complex isolated was reduced from the starting V(v) species and generated the V(iii) fully SST-substituted complex 11. This precursor was solved in a rigorous TBPY-5 geometry bound by three equatorial SST ligands and two axial py molecules.

Switching to the larger congener Nb yielded monomeric 12. The exact TBPY-5 geometry for the Nb atom occurs through the coordination of three SST and two OEt ligands. One attempt at increasing the SST substitution in py led to an unusual hydrolyzed species, 13, where an oxo ligand is trans to a coordinated py molecule. This monomeric species is tri-substituted by SST ligands where the Nb metal center adopts a TBPY-5 geometry. The source of the oxo ligand is not understood at this point but it is believed to be either due to adventitious water or reduction of OR, which is often reported in the formation of oxo species. See D. C. Bradley et al., *Alkoxo and Aryloxo Derivatives of Metals,* Academic Press: San Diego (2001); and N. Y. Turova et al., *The Chemistry of Metal Alkoxides,* Kluwer Academic Publishers: Boston (2002).

An alternative oxidized species was identified, forming the cluster 14. For this complex, there are six Nb atoms arranged in an OC-6 geometry around a $\mu_6$-O atom. Each Nb octahedron is also bridged by four oxo ligands so that each Nb atom has an oxo bridge to four neighboring Nb atoms. The final OC-6 coordination site is occupied via a terminal SST ligand. Based on charge balance there are two missing positive charges. The protons are assumed to be bound to the bridging oxo ligands and disordered over the 12 possible sites. These disordered H atoms are indicated by parentheses outside of the molecular formula.

From another reaction of [Nb(OEt)$_5$] with H-SST, a single crystal was identified as [Nb$_8$O$_{10}$(OEt)$_{18}$(SST)$_2$·⅓Na$_2$O] (15). The mechanism concerning the formation of this compound is not known, but the Na$_2$O may be a remnant of incomplete H-SST drying (i.e., H$_2$O and Na$_2$SO$_4$ may have been present during this preparation). The structural arrangement of 15 consists of a plane of five Nb metals each of which is OC-6. Above and below this plane are a set of Nb and Na atoms that also have an OC-6 geometry. A terminal SST ligand is coordinated to Nb(1). Atoms Nb(2) and Nb(4) each possess a terminal OEt molecule. Nb(2) and Nb(4) also have three $\mu$-OEt molecules that bridge a Nb atom in plane, a Nb atom out of plane, and a Na atom. Additionally, five $\mu$-oxo ligands complete the coordination that form this structure.

The mono-substituted, Ta derivative 16 was solved as a dinuclear complex. The distorted OC-6 bound Ta metal centers employ one SST and four OEt as terminal ligands and two $\mu$-OEt ligands to fill their coordination sites. As more SST ligands are introduced the mononuclear complex 17 was isolated using three SST and two OEt ligands. The geometry around the Ta metal center for 17 was found to be TBPY-5.

The preferential formation of the monomeric SST-substituted compounds noted above was attributed to the steric bulk of the SST, with dinuclear complex 16 isolated only at lower SST-substitution. The metal ligand distances of 2-17 fall within relatively small ranges (M-O(SST) from 1.77-2.02 Å and M-OR from 1.75-1.95 Å). The angles around the metals were solved in slightly distorted T-4 (2-5 and 7-9), TBPY-5 (6, 10-13, 17), and OC-6 (14-16). Since there is a dearth of SST/OR derivatives that can be reasonably used as model complexes for metrical comparisons, the appropriate siloxide derivatives were evaluated instead.

Thermal Conversion of SST-Modified Metal Alkoxide [M(SST)$_n$(OR)$_{x-n}$] Precursors Thermal gravimetric analyses were undertaken for each product to determine the SST versus OR decomposition temperatures. For complexes 2-4 and 9-11 a single weight loss was noted in the TGA/DSC curves of these complexes; whereas, for 5-8, 12, 13, 16, and 17, multiple decomposition steps were noted. This latter behavior is of particular interest, as different parts of the different ligands might be selectively removed through a thermal process.

Figure 18:
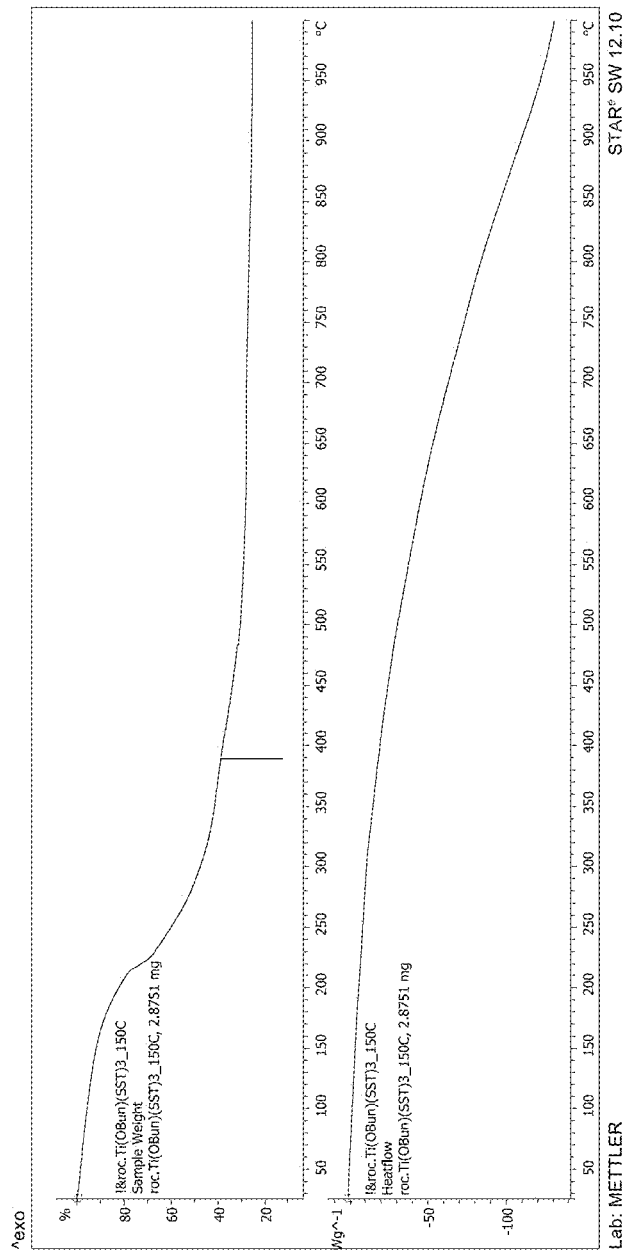
FIG. 18 is a TGA/DSC curve of compound 5 [(SST)$_3$Ti (OBu")].
Figure 19A:
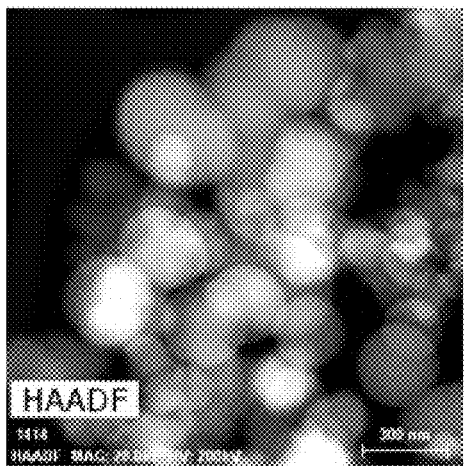
FIGS. 19(a)-(c) are STEM HAADF images of thermal processed (a) 5, (b) 6, and (c) 9.
Figure 19D:
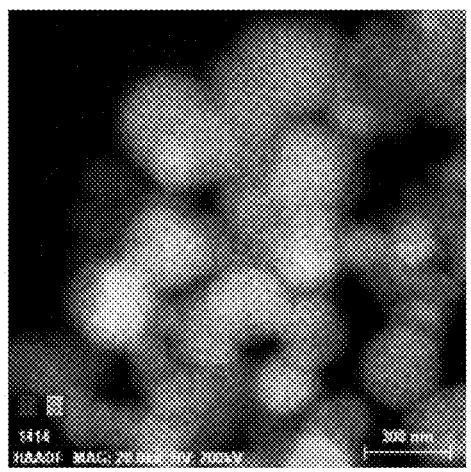
FIGS. 19(d)-(f) are EDS maps of thermal processed (d) 5, (e) 6, and (f) 9.
Figure 19B:
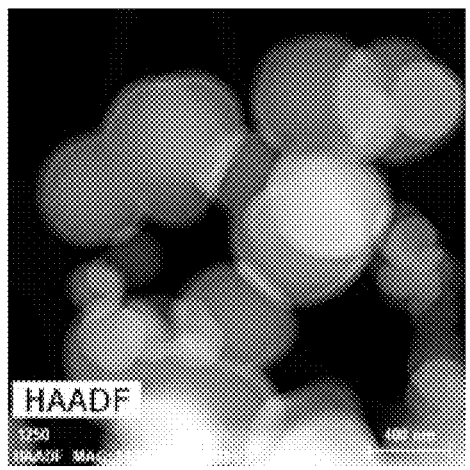
Figure 19E:
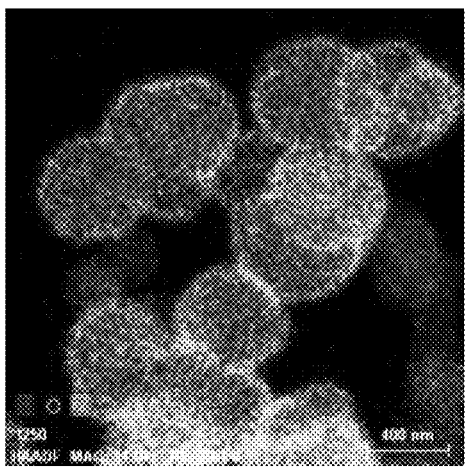
Figure 19C:
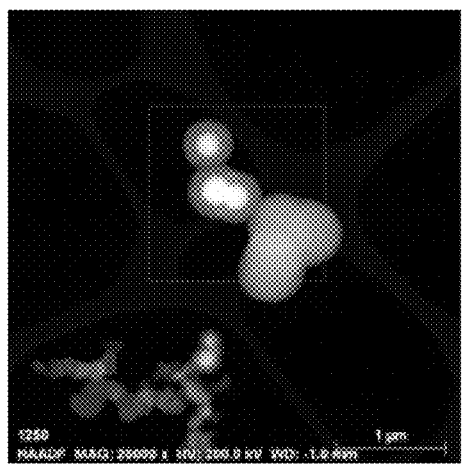
Figure 19F:
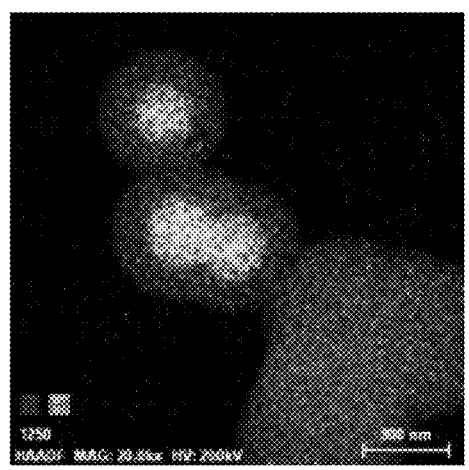

Based on these results, initial efforts focused on the conversion of the tri-SST complex 5 to generate the desired MSiO$_x$. The TGA/DSC graph for compound 5 is shown in FIG. 18. For processing of 5, the powder was thermally annealed in a box furnace in a hood under circumjacent atmospheres. The dried bulk powder was placed into a pre-fired ceramic boat and heated under ambient temperatures to 450° C. for 3 h. The PXRD pattern was collected and the resulting powder was found to be amorphous. The cycle was repeated at various 100° C. intervals (i.e., 550, 650° C., etc.) and each PXRD pattern proved to be amorphous. The sample was ultimately fired at 1100° C. and minor peaks associated with TiO$_2$ (titanium oxide) were noted. A similar process was used for the other samples and heating was suspended upon successful PXRD characterization of a ceramic phase: 6 (850° C., 3 h, cristobalite—SiO$_2$ and zirconium silicate—ZrSiO$_4$); 9 (550° C., 4 h, stishovite—SiO$_2$ and hafnium oxide—HfO$_2$); 11 (750° C., 8 h, cristobalite—SiO$_2$ and vanadium oxide—V$_2$O$_3$); 12 (700° C., 12 h, stishovite and niobium oxide—Nb$_2$O$_3$); and 16 (700° C., 12 h, stishovite and tantalum oxide—Ta$_2$O$_3$). The majority of samples had extremely broad PXRD patterns that reflect the nanocrystalline nature of the metal oxides and additional amorphous material.

After thermal treatment and subsequent PXRD characterization, the samples were analyzed by TEM to assist in determining why the samples did not readily form the expected MO$_x$ or MSiO$_x$ phases. FIGS. 19($a$)-($f$) (compounds 5, 6, and 9) and 20($a$)-($e$) (compounds 11, 12, and 16) show the STEM HAADF images and EDS maps obtained for select processed samples. As expected with these high content siloxide complexes, a substantial amount of SiO$_2$ material was observed but additional, unusual structural arrangements were also observed. For the particle generated from 5, a silica particle approaching 250 nm was 'sprinkled' with TiO$_2$ nanoparticles (FIGS. 19(a) and (d)). In contrast, 300 nm SiO$_2$@ZrO$_2$ (core@shell) structures were observed for the particles generated from 6 (FIGS. 19(b) and (e)). Further, the particle generated from 9 yielded the opposite arrangement having a SiO$_2$ shell with a HfO2 core as noted in FIGS. 19(c) and (f). The TEM images confirmed that the broad regions noted in the PXRD patterns were related to amorphous SiO$_2$ (core/shell) matrices, as opposed to phase separated ceramics. The ability to form these unusual ceramic/glass arrangements from a single-source precursor is unprecedented. See R. G. Chaudhuri and S. Paria, *Chem. Rev.* 112, 2373 (2012); and M. B. Gawande et al., *Chem. Soc. Rev.* 44, 7540 (2015). The factors controlling the formation of inter-dispersed MO$_2$ or the core@shell arrangements with the ceramic MO$_2$ and SiO$_2$ being either the core or the shell include the processing temperature and the solubility of the metal oxide in the 'glass' matrix.

Figure 20A:
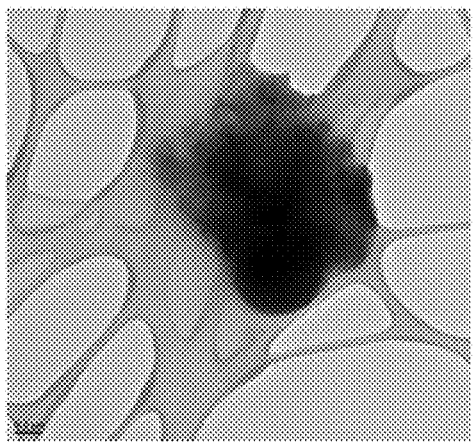
FIGS. 20(a)-(c) are STEM HAADF images of thermal processed (a) 11, (b) 12, and (c) 16.
Figure 20B:
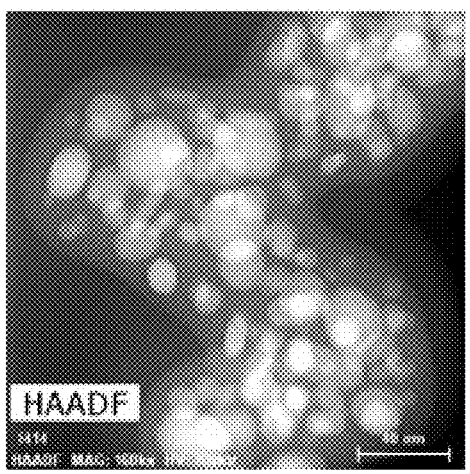
Figure 20D:
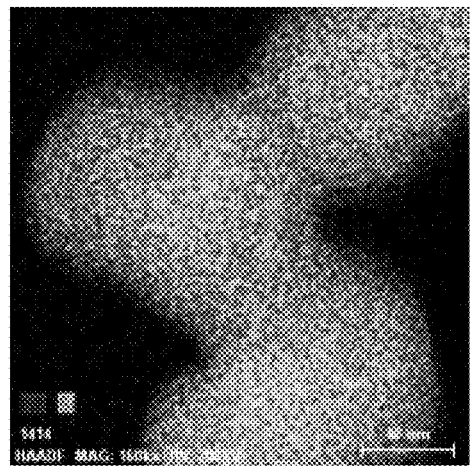
FIGS. 20(d)-(e) are EDS maps of thermal processed (d) 12 and (e) 16.
Figure 20C:
Figure 20E:

The STEM HAADF images and EDS maps of material isolated from the thermal processing of compounds 11, 12, and 16 are shown in FIGS. 20(a)-(e). The material isolated for 11 was found to be large spherical, as shown in FIG. 20(a)). An irregular shaped vanadium oxide with a silica matrix is present. Attempts to generate a map of the final material was not undertaken since the particles were not well defined and distributed. An interesting continuous matrix of SiO$_2$ (90-100 nm width) with large niobium oxide (5-35 nm) nanoparticles were noted for the larger congener 12, as shown in FIGS. 20(b) and (d). This arrangement was not noted in the previous TEM images. Finally, for 16, the Ta material resembles the 'sprinkle' arrangement reported for the Ti species but with tantalum oxide spread throughout the SiO$_2$ matrix, as shown in FIGS. 20(c) and (e).

The extended network of SiO$_2$ observed in most of these samples indicates the hydrolysis of the SST ligand occurs rapidly with the high processing temperature facilitating the formation of the ceramic oxide component. The premature hydrolysis of the SST component may be the main reason for the phase separation (i.e., MO$_x$ and SiO$_2$ formation) observed. The solubility of the different MO$_x$ ceramics in the 'glass' matrix will dictate whether the ceramic acts as a core or shell or if it remains inter-dispersed in the SiO$_2$. It is expected that with proper tuning of the thermal processing, these Group 5 derivatives with form core-shell nanoparticles as well.

In separate experiments, these unusual architectures have already demonstrated some unusual benefits. The core/shell structures may contribute to increased radiation tolerance in nanoparticles due to their ability to prevent sputtering and either store displacement defects and implanted helium or allow it to diffuse out of their structure. In particular, the HfO$_2$/SiO$_2$ core/shell nanoparticles have demonstrated resistance to damage in extreme irradiation and thermal environments. Coupled with the proven functionality of HfO$_2$ in radiation therapy dose enhancement, this suggests that the core/shell structure may show promise for future cancer therapy concepts and micro-electronics design for radiation environments.

The present invention has been described as the single-source synthesis of ceramic oxide nanoparticles. It will be understood that the above description is merely illustrative of the applications of the principles of the present invention, the scope of which is to be determined by the claims viewed in light of the specification. Other variants and modifications of the invention will be apparent to those of skill in the art.

TABLE 1

Data collection parameters for compounds 1a-17.

| | Compound | | | | |
|---|---|---|---|---|---|
| | 1a | 2 | 3 | 4 | 5 |
| Chem. Form. | $C_{33}H_{100}ClNO_3Si_{12}$ | $C_{24}H_{68}O_4Si_8Ti$ | $C_{26}H_{72}O_4Si_8Ti$ | $C_{53.04}H_{143.30}O_8Si_{16}Ti_2$ | $C_{31}H_{90}O_4Si_{12}Ti$ |
| FW | 931.66 | 693.4 | 721.45 | 1454.72 | 912 |
| Temp (K) | 100.0 (2) | 100.0 (2) | 100.0 (2) | 100.0 (2) | 100.0 (2) |
| Space Group | triclinic | orthorhombic | triclinic | monoclinic | triclinic |
| | P-1 | P 21 21 21 | P-1 | P 1 21/C 1 | P-1 |
| a (Å) | 9.4066 (8) | 9.6811 (10) | 9.970 (3) | 20.4782 (9) | 10.4545 (8) |
| b (Å) | 14.4997 (13) | 19.006 (3) | 17.906 (5) | 20.1102 (10) | 13.7169 (10) |
| c (Å) | 23.353 (2) | 23.564 (3) | 25.956 (7) | 24.3199 (11) | 20.4786 (15) |
| α (deg) | 91.298 (7) | | 88.473 (10) | | 91.432 (4) |
| β (deg) | 90.390 (7) | | 80.126 (10) | 104.038 (2) | 92.465 (5) |
| γ (deg) | 104.658 (6) | | 89.730 (11) | | 99.895 (4) |
| V (Å$^3$) | 3080.5 (5) | 4335.7 (9) | 4564 (2) | 9716.3 (8) | 2888.8 (4) |
| Z | 2 | 4 | 4 | 4 | 2 |
| D$_{calcd}$(Mg/m$^3$) | 1.004 | 1.062 | 1.05 | 0.994 | 1.048 |
| μ(Mo, Kα) (mm$^{-1}$) | 0.322 | 0.442 | 0.422 | 0.397 | 0.424 |
| R1$^a$ (%) (all data) | 9.95 (19.34) | 2.37 (2.76) | 13.06 (24.63) | 9.05 (19.32) | 9.95 (14.93) |
| wR2$^b$ (%) (all data) | 27.88 (36.18) | 5.57 (5.76) | 29.48 (35.93) | 22.49 (28.82) | 28.96 (32.45) |

| | Compound | | | | |
|---|---|---|---|---|---|
| | 6 | 7 | 8 | 9 | 10a |
| Chem. Form. | $C_{31}H_{77}NO_4Si_8Zr$ | $C_{31}H_{90}O_4Si_{12}Zr$ | $C_{30}O_4Si_{11.99}Zr$ | $C_{26}H_{72}HfO_4Si_8$ | $C_{33}H_{81}HfNO_4Si_8$ |
| FW | 843.87 | 955.32 | 864.16 | 852.04 | 959.19 |
| Temp (K) | 100.0 (2) | 100.0 (2) | 100.0 (2) | 100.0 (2) | 100.0 (2) |
| Space Group | triclinic | Triclinic | orthorhombic | monoclinic | monoclinic |
| | P-1 | P-1 | P b c a | P 1 21/n 1 | P 1 21/n 1 |
| a (Å) | 15.072 (2) | 13.6031 (15) | 14.1859 (5) | 10.049 (3) | 21.5889 (7) |
| b (Å) | 17.810 (2) | 14.2299 (16) | 22.9062 (8) | 18.214 (6) | 24.6747 (8) |
| c (Å) | 18.970 (2) | 18.109 (2) | 36.8870 (14) | 25.960 (9) | 21.9870 (6) |
| α (deg) | 86.890 (3) | 73.700 (3) | | | |
| β (deg) | 88.874 (3) | 81.479 (3) | | 100.921 (9) | 116.9780 (10) |
| γ (deg) | 83.103 (5) | 62.362 (3) | | | |

TABLE 1-continued

Data collection parameters for compounds 1a-17.

| V (Å$^3$) | 5047.7 (11) | 2979.9 (6) | 11986.2 (7) | 4665 (3) | 10437.9 (6) |
|---|---|---|---|---|---|
| Z | 4 | 2 | 8 | 4 | 8 |
| D$_{calcd}$(Mg/m$^3$) | 1.11 | 1.065 | 0.958 | 1.213 | 1.221 |
| μ (Mo, Kα) (mm$^{-1}$) | 0.436 | 4.027 | 0.445 | 2.465 | 2.212 |
| R1$^a$ (%) (all data) | 3.74 (5.16) | 5.36 (5.76) | 9.65 (18.05) | 7.88 (18.58) | 4.67 (10.46) |
| wR2$^b$ (%) (all data) | 8.98 (9.82) | 13.40 (13.66) | 26.33 (34.04) | 12.28 (14.95) | 7.35 (9.13) |

| | Compound | | | | |
|---|---|---|---|---|---|
| | 10b | 11 | 12 | 13 | 14 |
| Chem. Form. | C$_{38}$H$_{86}$HfN$_2$O$_4$Si$_8$ | C$_{37}$H$_{91}$N$_2$O$_3$Si$_{12}$V | C$_{27.22}$NbO$_5$Si$_{12}$ | C$_{32}$H$_{86}$NNbO$_4$Si$_{12}$ | C$_{54}$H$_{162}$Nb$_6$O$_{19}$Si$_{24}$ |
| FW | 1038.29 | 1000.13 | 836.85 | 979.00 | 2347.45 |
| Temp (K) | 100.0 (2) | 100.0 (2) | 100.0 (2) | 100.0 (2) | 100.0 (2) |
| Space Group | orthorhombic P b c a | triclinic P-1 | hexagonal P 63 | monoclinic P 1 21/c 1 | trigonal R-3 |
| a (Å) | 15.5453 (10) | 14.2904 (15) | 14.2009 (7) | 22.5219 (12) | 15.6974 (6) |
| b (Å) | 19.5393 (12) | 14.2961 (14) | 14.2009 (7) | 10.0264 (5) | 15.6974 (6) |
| c (Å) | 36.861 (2) | 17.3683 (17) | 16.6094 (12) | 25.7689 (14) | 42.577 (3) |
| α (deg) | | 89.771 (4) | 90 | 90 | 90 |
| β (deg) | | 89.945 (4) | 90 | 90.060 (2) | 90 |
| γ (deg) | | 60.378 (3) | 120 | | 120 |
| V (Å$^3$) | 11196.4 (12) | 3084.5 (5) | 2900.8 (3) | 5819.0 (5) | 9085.8 (9) |
| Z | 8 | 2 | 1.99998 | 4 | 3 |
| D$_{calcd}$(Mg/m$^3$) | 1.232 | 1.077 | 0.958 | 1.118 | 1.287 |
| μ(Mo, Kα) (mm$^{-1}$) | 2.068 | 0.424 | 0.477 | 0.483 | 7.126 |
| R1$^a$ (%) (all data) | 3.53 (7.7) | 9.93 (13.14) | 9.79 (11.64) | 6.94 (14.27) | 6.23 (6.4) |
| wR2$^b$ (%) (all data) | 6.83 (8.64) | 23.29 (24.97) | 26.81 (29.71) | 17.04 (22.40) | 15.67 (15.81) |

| | Compound | | | | |
|---|---|---|---|---|---|
| | 15 | 16 | 17 | [V(O)(SST)$_2$(OEt)] | [V(OPr$^i$)$_2$(SST)$_3$] |
| Chem. Form. | C$_{61}$NaNb$_8$O$_{30.50}$Si$_8$ | C$_{34}$H$_{94}$O$_{10}$Si$_8$Ta$_2$ | C$_{27.21}$O$_5$Si$_{12}$Ta | C$_{80}$H$_{240}$O$_{16}$Si$_{32}$V$_4$ | C$_{264}$H$_{720}$O$_{40}$Si$_{96}$V$_8$ |
| FW | 2211.6 | 1249.71 | 924.82 | 2561.244 | 7640.229 |
| Temp (K) | 100.0 (2) | 100.0 (2) | 100.0 (2) | 100.0 (2) | 100.0 (2) |
| Space Group | monoclinic C 1 2/c 1 | monoclinic P 1 21/c 1 | hexagonal P 63 | triclinic P(-1) | monoclinic C 2/c |
| a (Å) | 22.212 (5) | 23.1516 (12) | 14.2170 (8) | 13.7593 (26) | 13.805 (3) |
| b (Å) | 15.064 (4) | 13.3040 (5) | 14.2170 (8) | 16.5268 (35) | 23.944 (5) |
| c (Å) | 30.053 (7) | 18.7570 (10) | 16.6716 (14) | 18.0566 (35) | 32.371 (8) |
| α (deg) | | 90 | 90 | 88.1062 (75) | |
| β (deg) | 100.939 (9) | 95.0452 (19) | 90 | 89.9146 (67) | 91.261 (7) |
| γ (deg) | | 90 | 120 | 74.3637 (68) | |
| V (Å$^3$) | 9873 (4) | 5754.9 (5) | 2918.3 (4) | 3951.79 | 10697.7 |
| Z | 4 | 4 | 2 | 4 | 8 |
| D$_{calcd}$(Mg/m$^3$) | 1.488 | 1.442 | 1.052 | | |
| μ(Mo, Kα) (mm$^{-1}$) | 1.059 | 4.007 | 2.152 | | |
| R1$^a$ (%) (all data) | 9.66 (26.32) | 3.99 (6.58) | 5.63 (6.65) | 16.46 | 21.85 |
| wR2$^b$ (%) (all data) | 20.56 (28.13) | 8.1 (8.91) | 16.22 (17.38) | | |

$^a$R1 = Σ ||F$_o$| − |F$_c$||/Σ |F$_o$| × 100
$^b$wR2 = [Σ w (F$_o^2$ − F$_c^2$)$^2$/Σ (w |F$_o$|$^2$)$^2$]$^{1/2}$ × 100

We claim:

1. A method to synthesize a metal-siloxide precursor, comprising reacting tris(trimethylsilyl)silanol ligand (H-SST) with a Group 4 or 5 metal alkoxide in a solvent to form an SST-modified metal alkoxide precursor.

2. The method of claim 1, wherein the Group 4 metal comprises Ti, Zr, or Hf.

3. The method of claim 1, wherein the Group 5 metal comprises V, Nb, or Ta.

4. The method of claim 1, wherein the alkoxide comprises OCH$_2$CH$_3$, OCHMe$_2$, or OCMe$_3$, or OCH$_2$CMe$_3$.

5. The method of claim 1, wherein the solvent comprises toluene or pyridine.

6. The method of claim 2, wherein the SST-modified metal siloxide precursor comprises [Ti(SST)$_2$(OR)$_2$], wherein OR=OPr$^i$, OBu$^t$, or ONep; [Ti(SST)$_3$(OBu$''$)]; [Zr(SST)$_2$(OBu$^t$)$_2$(py)]; [Zr(SST)$_3$(OR)], wherein OR=OBu$^t$ or ONep; or [Hf(SST)$_2$(OBu$^t$)$_2$]; [Hf(SST)$_2$(ONep)$_2$(py)$_n$], wherein n=1 or 2, and wherein OPr$^i$=OCH(CH$_3$)$_2$, OBu$^t$=OC(CH$_3$)$_3$, OBu$''$=O(CH$_2$)$_3$CH$_3$, ONep=OCH$_2$C (CH$_3$)$_3$, and py=pyridine.

7. The method of claim 3, wherein the SST-modified metal siloxide precursor comprises [V(SST)$_3$(py)$_2$]; [Nb (SST)$_3$(OEt)$_2$]; [Nb(O)(SST)$_3$(py)]; 2[H][(Nb(μ-O)$_2$ (SST))$_6$(μ$_6$-O)]; [Nb$_8$O$_{10}$(OEt)$_{18}$(SST)$_2$·⅕Na$_2$O]; [Ta(SST) (μ-OEt)(OEt)$_3$]$_2$; or [Ta(SST)$_3$(OEt)$_2$]; wherein OEt=OCH$_2$CH$_3$ and py=pyridine.

8. A method of making a ceramic oxide nanoparticle comprising heating the SST-modified metal alkoxide precursor of claim 1 to above a decomposition temperature.

9. The method of claim 8, wherein the decomposition temperature is greater than or equal to 450° C.

10. The method of claim 8, wherein the ceramic oxide nanoparticle comprises a core-shell nanoparticle.

11. The method of claim 10, wherein the core-shell nanoparticle comprises a silicate core and a metal oxide shell.

12. The method of claim 11, wherein the metal oxide shell comprises $ZrO_2$.

13. The method of claim 10, wherein the core-shell nanoparticle comprises a metal oxide core and a silicate shell.

14. The method of claim 13, wherein the metal oxide core comprises $HfO_2$.

15. The method of claim 8, wherein the ceramic oxide nanoparticle comprises $TiO_2$, $Ta_2O_3$, $Nb_2O_3$, or $V_2O_3$.

* * * * *